United States Patent
Zuker et al.

(10) Patent No.: US 7,087,388 B1
(45) Date of Patent: Aug. 8, 2006

(54) COMPOSITIONS AND METHODS FOR IDENTIFYING MODULATORS OF TRANSDUCISOMES, A NEW CLASS OF THERAPEUTIC TARGETS

(75) Inventors: Charles S. Zuker, San Diego, CA (US); John D. Mendlein, Encinitas, CA (US); Yumei Sun, Newton, MA (US); Susan Tsunoda, San Diego, CA (US); Jimena Sierralta, Santiago (CL)

(73) Assignee: Aurora Biosciences Corporation, San Diego, CA (US)

( * ) Notice: Subject to any disclaimer, the term of this patent is extended or adjusted under 35 U.S.C. 154(b) by 0 days.

(21) Appl. No.: 09/462,517

(22) PCT Filed: Jul. 15, 1998

(86) PCT No.: PCT/US98/14667

§ 371 (c)(1),
(2), (4) Date: May 18, 2000

(87) PCT Pub. No.: WO99/03974

PCT Pub. Date: Jan. 28, 1999

Related U.S. Application Data

(60) Provisional application No. 60/052,588, filed on Jul. 15, 1997.

(51) Int. Cl.
*G01N 33/53* (2006.01)
*C07K 14/00* (2006.01)

(52) U.S. Cl. .................. 435/7.1; 435/69.1; 530/350
(58) Field of Classification Search .................. 435/7.1, 435/69.1; 530/350
See application file for complete search history.

(56) References Cited

U.S. PATENT DOCUMENTS 6,001,575 A * 12/1999 Huganir et al. ................. 435/6
6,004,808 A * 12/1999 Negulescu et al. ......... 435/325

OTHER PUBLICATIONS

Shieh et al. 1995; Neuron 14:201–210.*
Armin Huber et al, The transient receptor potential protein (Trp), a putative store–operated Ca 2+ channel essential for phosphoinositide–mediated photoreception, forms, a signaling complex with NorpA, InaC and InaD, The EMBO vol. 15 No. 24, pp. 7036–7045, 1996.*
Brenman, J.E. et al., "Interaction of nitric oxide synthase with the postsynaptic density protein PSD–95 and alpha1–syntrophin mediated by PDZ domains", *Cell*, vol. 84, 757–767, 1996.
Cabral, J.H. et al., "Crystal structure of a PDZ domain", *Nature*, vol. 382, 649–652, 1996.
Chevesich, J et al, "Requirement for the PDZ domain protein, INAD, for localization of the TRP store–operated channel to a signaling complex", *Neuron*, vol. 18, 95–105, 1997.
Choi, K.Y. et al., "Ste5 tethers multiple protein kinases in the MAP kinase cascade required for mating in *S. cerevisiae*", *Cell*, vol. 78, 499–512, 1994.
Dong, H. et al., "GRIP: a synaptic PDZ domain–containing protein that interacts with AMPA receptors", *Nature* vol. 386, 279–284, 1997.
Doyle, D.A. et al, "Crystal structure of a complexed and peptide–free membrane protein–binding domain: molecular basis of peptide recognition by PDZ", *Cell*, vol. 85, 1067–1076, 1996.
Fanning, A.S. & Anderson, J.M., "Protein–protein interactions: PDZ domain networks", *Curr Biol*, vol. 6, 1385–1388, 1996.
Harrison, S.C., "Peptide–surface association: the case of PD and PTB domains", *Cell* vol. 86, 341–343 1996.
Kim, E. et al., "GKAP, a novel synaptic protein that interacts with the guanylate kinase–like doain of the PSD095/SAP90 family of channel clustering molecules", J. Cell Biol, vol. 136, 669–678, 1997.
Kim, E. & Sheng, M., "Differential K+ channel clustering activity of PSD–95 and SAP97, two related membrane–associated putative guanylate kinases", *Neuropharmacology*, vol. 35, 993–1000, 1996.
Larrivee, D.C. et al., "Mutation that selectively affects rhodopsin concentration in the peripheral photoreceptors of Drosophilia melanogaster", *Journal of General Physiology*, vol. 78, 521–545, 1981.
Marcus, S. et al., "Complexes between STE5 and components of the pheromon–responsive mitogen–activated protein kinase module", *Proc Natl Acad Sci USA*, vol. 91, 7762–7766, 1994.

(Continued)

*Primary Examiner*—Karen Cochrane Carlson
(74) *Attorney, Agent, or Firm*—DLA Piper Rudnick Gray Cary US LLP

(57) ABSTRACT

The invention provides cells and methods for identifying modulators of signal transduction, based on transducisome proteins that coordinate and assemble many types of signal transduction proteins. A transducisome is a PDZ domain containing protein that binds at least one signal transduction protein or a PDZ domain containing protein with at least one signal transduction protein bound. Examples of transducisome proteins include INAD, GRIP and other recently identified multi-PDZ domain proteins. Examples of signal transduction proteins include GPCRs, tyrosine kinase receptors, tyrosine phosphatase receptors, ion channels, phospholipases, adenylate cyclases, kinases and G-proteins. Also provided are methods for identifying modulators of signal transduction, proteins (and polynucleotides encoding the same) corresponding to transducisomes, modified transducisomes or defective transducisomes to use in assays of signal transduction, and a screening assay system for detecting protein-protein interactions.

10 Claims, 7 Drawing Sheets

OTHER PUBLICATIONS

Printen, J.A. & Sprague, G.J., "Protein–protein interactions in the yeast pheromone response pathway: Ste5p interacts with all members of the MAP kinase cascade", *Genetics*, vol. 609–619, 1994.

Saras, J. & Heldin, C.H., "PDZ domains bind carboxy–terminal sequences of target proteins.", *Trendas Biochem Sci*, vol. 21, 445–458, 1996.

Sato, T. et al, "FAP–1: a protein tyrosine phosphatase that associates with Fas", *Science* vol. 268, 411–0415, 1995.

Schlessinger, J., "SH2/SH3 signaling proteins", *Curr Opin Genet Dev*, vol. 4, 25–30, 1994.

Scott, K. et al, "Gaz Protein Function in vivo: Genetic Dissectio nof Its Role in Photoreceptor Cell Physiology", *Neuron*, Kim, E. & Sheng, M., "Differential K+ channel clustering activity of PSD–95 and SAP97, two related membrane–associated putative guanylate kinases", *Neuropharmacology*, vol. 15, 919–927, 1995.

Sheng, M., "PDZs and receptor/channel clustering: rounding up the latest suspects.", *Neuron*, vol. 17, 575–578, 1996.

Shieh, B.–H. & Zhu, M.Y., "Regulation of the TRP Ca2+ channel by INAD in Drosophila photoreceptors", *Neuron*, vol. 16, 991–998, 1996.

Shieh et al, "Association of INAD with NORPA is essential for controlled activation and deactivation of Drosophilia phototransduction in vivo", *Proceedings of the Natioanl Academy of Science USA*, vol. 94, 12682–12687, 1997.

Songyang, Z et al, "Recognition of unique carboxyl–terminal motifs by distinct PDZ domains", *Science*, vol. 275, 73–77, 1997.

Smith, D.P. et al, "Photoreceptor deactivation and retinal degeneration mediated by a photoreceptor–specific protein kinase C", *Science*, vol. 254, 1478–1484, 1991.

Tsunoda et al., "A multivalent PDZ–domain protein assembles signaling complexes in a G–protein–coupled cascade", *Nature*, vol. 388, 243–249, 1997.

van der Geer, P & Pawson, T., "The PTB domain: a new protein module implicated in signal transduction", *Trends Biochem Sci*, vol. 20, 227–280, 1995.

Woods, D.F. & Bryant, P.J., "The discs–large tumor suppressor gene of Drosophila encodes a guanylate kinase homolog localized at septate junctions.", *Cell*, vol. 66, 451–464, 1991.

\* cited by examiner

SEQUENCE LISTING

```
<160> NUMBER OF SEQ ID NOS:   16

<210> SEQ ID NO 1
<211> LENGTH: 674
<212> TYPE: PRT
<213> ORGANISM: Drosophila melanogaster

<400> SEQUENCE: 1

Met Val Gln Phe Leu Gly Lys Gln Gly Thr Ala Gly Glu Leu Ile His
1               5                   10                  15

Met Val Thr Leu Asp Lys Thr Gly Lys Lys Ser Phe Gly Ile Cys Ile
                20                  25                  30

Val Arg Gly Glu Val Lys Asp Ser Pro Asn Thr Lys Thr Thr Gly Ile
            35                  40                  45

Phe Ile Lys Gly Ile Val Pro Asp Ser Pro Ala His Leu Cys Gly Arg
        50                  55                  60

Leu Lys Val Gly Asp Arg Ile Leu Ser Leu Asn Gly Lys Asp Val Arg
65                  70                  75                  80

Asn Ser Thr Glu Gln Ala Val Ile Asp Leu Ile Lys Glu Ala Asp Phe
                85                  90                  95

Lys Ile Glu Leu Glu Ile Gln Thr Phe Asp Lys Ser Asp Glu Gln Gln
                100                 105                 110

Ala Lys Ser Asp Pro Arg Ser Asn Gly Tyr Met Gln Ala Lys Asn Lys
            115                 120                 125

Phe Asn Gln Glu Gln Thr Thr Asn Asn Asn Ala Ser Gly Gly Gln Gly
        130                 135                 140

Met Gly Gln Gly Gln Gly Gln Gly Gln Gly Met Ala Gly Met Asn Arg
145                 150                 155                 160

Gln Gln Ser Met Gln Lys Arg Asn Thr Thr Phe Thr Ala Ser Met Arg
                165                 170                 175
```

```
Gln Lys His Ser Asn Tyr Ala Asp Glu Asp Asp Glu Asp Thr Arg Asp
            180                 185                 190

Met Thr Gly Arg Ile Arg Thr Glu Ala Gly Tyr Glu Ile Asp Arg Ala
            195                 200                 205

Ser Ala Gly Asn Cys Lys Leu Asn Lys Gln Glu Lys Asp Arg Asp Lys
            210                 215                 220

Glu Gln Glu Asp Glu Phe Gly Tyr Thr Met Ala Lys Ile Asn Lys Arg
225                 230                 235                 240

Tyr Asn Met Met Lys Asp Leu Arg Arg Ile Glu Val Gln Arg Asp Ala
                245                 250                 255

Ser Lys Pro Leu Gly Leu Ala Leu Ala Gly His Lys Asp Arg Gln Lys
            260                 265                 270

Met Ala Cys Phe Val Ala Gly Val Asp Pro Asn Gly Ala Leu Gly Ser
            275                 280                 285

Val Asp Ile Lys Pro Gly Asp Glu Ile Val Glu Val Asn Gly Asn Val
            290                 295                 300

Leu Lys Asn Arg Cys His Leu Asn Ala Ser Ala Val Phe Lys Asn Val
305                 310                 315                 320

Asp Gly Asp Lys Leu Val Met Ile Thr Ser Arg Arg Lys Pro Asn Asp
                325                 330                 335

Glu Gly Met Cys Val Lys Pro Ile Lys Lys Phe Pro Thr Ala Ser Asp
            340                 345                 350

Glu Thr Lys Phe Ile Phe Asp Gln Phe Pro Lys Ala Arg Thr Val Gln
            355                 360                 365

Val Arg Lys Glu Gly Phe Leu Gly Ile Met Val Ile Tyr Gly Lys His
            370                 375                 380

Ala Glu Val Gly Ser Gly Ile Phe Ile Ser Asp Leu Arg Glu Gly Ser
385                 390                 395                 400

Asn Ala Glu Leu Ala Gly Val Lys Val Gly Asp Met Leu Leu Ala Val
                405                 410                 415

Asn Gln Asp Val Thr Leu Glu Ser Asn Tyr Asp Asp Ala Thr Gly Leu
            420                 425                 430

Leu Lys Arg Ala Glu Gly Val Val Thr Met Ile Leu Leu Thr Leu Lys
            435                 440                 445

Ser Glu Glu Ala Ile Lys Ala Glu Lys Ala Ala Glu Lys Lys Lys
            450                 455                 460

Glu Glu Ala Lys Lys Glu Glu Lys Pro Gln Glu Pro Ala Thr Ala
465                 470                 475                 480

Glu Ile Lys Pro Asn Lys Lys Ile Leu Ile Glu Leu Lys Val Glu Lys
                485                 490                 495

Lys Pro Met Gly Cys His Arg Leu Arg Arg Gln Lys Gln Pro Cys His
            500                 505                 510

Asp Trp Leu Cys Asn His Pro Arg Leu Ser Gly Gly Gln Val Ala Ala
            515                 520                 525

Asp Lys Arg Leu Lys Ile Phe Asp His Ile Cys Asp Ile Asn Gly Thr
            530                 535                 540

Pro Ile His Val Gly Ser Met Thr Thr Leu Lys Val His Gln Leu Phe
545                 550                 555                 560

His Thr Thr Tyr Glu Lys Ala Val Thr Leu Thr Val Phe Arg Ala Asp
                565                 570                 575

Pro Pro Glu Leu Glu Lys Phe Asn Val Asp Leu Met Lys Lys Ala Gly
            580                 585                 590
```

```
Lys Glu Leu Gly Leu Ser Leu Ser Pro Asn Glu Ile Gly Cys Thr Ile
        595                 600                 605

Ala Asp Leu Ile Gln Gly Gln Tyr Pro Glu Ile Asp Ser Lys Leu Gln
    610                 615                 620

Arg Gly Asp Ile Ile Thr Lys Phe Asn Gly Asp Ala Leu Glu Gly Leu
625                 630                 635                 640

Pro Phe Gln Val Cys Tyr Ala Leu Phe Lys Gly Ala Asn Gly Lys Val
                645                 650                 655

Ser Met Glu Val Thr Arg Pro Lys Pro Thr Leu Arg Thr Glu Ala Pro
            660                 665                 670

Lys Ala

<210> SEQ ID NO 2
<211> LENGTH: 2059
<212> TYPE: DNA
<213> ORGANISM: Drosophila melanogaster

<400> SEQUENCE: 2
atggttcagt tcctgggcaa acagggcacc gcgggtgagc tcattcacat ggtgaccctg      60
gacaagacgg gcaagaagtc cttcggcatc tgcatagtgc gcggcgaggt gaaggattcg     120
cccaacacca agacaaccgg catcttcatc aagggcattg tgcccgacag tcccgcgcat     180
ctgtgtggtc gcctaaaggt tggcgatcgg atcctctcgc tcaacggaaa ggatgtgcgc     240
aactccaccg aacaggcggt catcgatctc atcaaggagg cggacttcaa gatcgagctg     300
gagattcaga ccttcgacaa gagcgatgag cagcaggcca gtcagatccg cggagcaat      360 ggctacatgc aggccaagaa caagttcaat caggagcaga ccaccaacaa caatgcgtcc     420
ggaggtcagg aatggggca aggtcagggt cagggtcagg aatggctgg catgaaccgg       480 cagcaatcga tgcagaagcg gaataccaca ttcacggcct cgatgcgtca aagcatagt      540 aactacgccg acgaggatga cgaggacacc cgggacatga ccggtcgcat tcgcacggag     600
gcgggttatg agatcgatcg agcctccgcc ggtaattgca aacttaataa gcaggaaaag     660
gatcgcgaca aggagcagga agatgaattt ggctacacga tggctaagat caacaagcgg     720
tacaacatga tgaaggatct cgcaggatc gaggtccaga gggacgccag caagccactg      780
ggactcgcac tcgctggcca caaggaccgc cagaagatgg cctgctttgt tgccggtgtg     840
gatcccaacg gagcattggg cagcgtggac attaagccgg cgacgagat cgtcgaggtc      900 aacggcaatg tgcttaagaa tcgctgccac ttgaacgcct ccgccgtgtt caagagcgtg     960
gatggggata agctcgtgat gatcacctcg cgacgcaagc ccaacgatga gggcatgtgc    1020
gtcaagccca tcaaaaagtt ccccaccgcg tctgatgaga ctaagtttat cttcgaccag    1080
tttcccaagg cgcgcacggt gcaggtgcgc aaggagggtt cctgggcatc atggtcatct    1140
atggcaagca cgctgaggtg ggcagtggca ttttcatctc ggatctgaga gagggatcga    1200
atgccgagtt ggcgggcgtg aaagtgggcg acatgctgct ggccgttaat caggatgtaa    1260
cactggaatc caactacgat gatgctactg gactgcttaa acgtgccgag gcgtagtga     1320 ccatgattct attgactctc aagagcgagg aggcgataaa ggctgagaag gcagcggaag    1380
agaaaaagaa ggaggaggcc aagaagagg ggaaaagcc acaggaaccc gccacagccg      1440
agatcaagcc gaacaaaaag atactcattg agttgaaggt ggaaaagaag ccaatgggcg    1500
tcatcgtctg cggcggcaag aacaaccatg tcacgactgg ctgtgtaatc acccacgttt    1560
atccggaggg acaagtggca gccgacaagc gcctcaagat ctttgaccac atttgtgata    1620
```

-continued

```
taaatggtac gccaatccac gtgggatcca tgacgacact gaaggtccat cagttattcc    1680
acaccacata cgagaaggcg gtcaccctaa cggtcttccg cgctgatcct ccggaactgg    1740
aaaagtttaa cgttgacctt atgaaaaaag caggcaagga gctgggcctg tcgctgtctc    1800
ccaacgaaat tggatgcacc atcgcggact tgattcaagg acaatacccg agattgaca    1860 gcaaactgca gcgcggcgat attatcacca attcaatggc gatgccttgg agggtcttcc    1920
gttccaggtg tgctacgcct tgttcaaggg agccaacgga aggtatcga tggaagtgac    1980 acgacccaag cccactctac gtacggaggc acccaaggcc tagagacgat cctcattctc    2040
ctctccgtag cgaagcagt                                                 2059
```

<210> SEQ ID NO 3
<211> LENGTH: 93
<212> TYPE: PRT
<213> ORGANISM: artificial
<220> FEATURE:
<223> OTHER INFORMATION: PSD-1

<400> SEQUENCE: 3

```
Met Glu Tyr Glu Glu Ile Thr Leu Glu Arg Gly Asn Ser Gly Leu Gly
1               5                   10                  15

Phe Ser Ile Ala Gly Gly Thr Asp Asn Pro His Ile Gly Asp Asp Pro
            20                  25                  30

Ser Ile Phe Ile Thr Lys Ile Ile Pro Gly Gly Ala Ala Ala Gln Asp
        35                  40                  45

Gly Arg Leu Arg Val Asn Asp Ser Ile Leu Phe Val Asn Glu Val Asp
    50                  55                  60

Val Arg Glu Val Thr His Ser Ala Ala Val Glu Ala Leu Lys Glu Ala
65                  70                  75                  80

Gly Ser Ile Val Arg Leu Tyr Val Met Arg Arg Lys Pro
                85                  90
```

<210> SEQ ID NO 4
<211> LENGTH: 93
<212> TYPE: PRT
<213> ORGANISM: Artificial
<220> FEATURE:
<223> OTHER INFORMATION: PSD95-2

<400> SEQUENCE: 4

```
Glu Lys Val Met Glu Ile Lys Leu Ile Lys Gly Pro Lys Gly Leu Gly
1               5                   10                  15

Phe Ser Ile Ala Gly Gly Val Gly Asn Gln His Ile Pro Gly Asp Asn
            20                  25                  30

Ser Ile Tyr Val Thr Lys Ile Ile Glu Gly Gly Ala Ala His Lys Asp
        35                  40                  45

Gly Arg Leu Gln Ile Gly Asp Lys Ile Leu Ala Val Asn Ser Val Gly
    50                  55                  60

Leu Glu Asp Val Met His Glu Asp Ala Val Ala Ala Leu Lys Asn Thr
65                  70                  75                  80

Tyr Asp Val Val Tyr Leu Lys Val Ala Lys Pro Ser Asn
                85                  90
```

<210> SEQ ID NO 5
<211> LENGTH: 87
<212> TYPE: PRT
<213> ORGANISM: artificial
<220> FEATURE:
<223> OTHER INFORMATION: PSD95-3

<400> SEQUENCE: 5

Arg Glu Pro Arg Arg Ile Val Ile His Arg Gly Ser Thr Gly Leu Gly
1               5                   10                  15

Phe Asn Ile Val Gly Gly Glu Asp Gly Glu Ile Phe Ile Ser Phe
            20                  25                  30

Ile Leu Ala Gly Gly Pro Ala Asp Leu Ser Gly Glu Leu Arg Lys Gly
        35                  40                  45

Asp Gln Ile Leu Ser Val Asn Gly Val Asp Leu Arg Asn Ala Ser His
    50                  55                  60

Glu Gln Ala Ala Ile Ala Leu Lys Asn Ala Gly Gln Thr Val Thr Ile
65                  70                  75                  80

Ile Ala Gln Tyr Lys Pro Glu
                85

<210> SEQ ID NO 6
<211> LENGTH: 87
<212> TYPE: PRT
<213> ORGANISM: artificial
<220> FEATURE:
<223> OTHER INFORMATION: dlg-3

<400> SEQUENCE: 6

Arg Glu Pro Arg Thr Ile Thr Ile Gln Lys Gly Pro Gln Gly Leu Gly
1               5                   10                  15

Phe Asn Ile Val Gly Gly Glu Asp Gly Gln Gly Ile Tyr Val Ser Phe
            20                  25                  30

Ile Leu Ala Gly Gly Pro Ala Asp Leu Gly Ser Glu Leu Lys Arg Gly
        35                  40                  45

Asp Gln Leu Leu Ser Val Asn Asn Val Asn Leu Thr His Ala Thr His
    50                  55                  60

Glu Glu Ala Ala Gln Ala Leu Lys Thr Ser Gly Gly Val Val Thr Leu
65                  70                  75                  80

Leu Ala Gln Tyr Arg Pro Glu
                85

<210> SEQ ID NO 7
<211> LENGTH: 88
<212> TYPE: PRT
<213> ORGANISM: artificial
<220> FEATURE:
<223> OTHER INFORMATION: nNOS

<400> SEQUENCE: 7

Pro Asn Val Ile Ser Val Arg Leu Phe Lys Arg Lys Val Gly Gly Leu
1               5                   10                  15

Gly Phe Leu Val Lys Glu Arg Val Ser Lys Pro Pro Val Ile Ile Ser
            20                  25                  30

Asp Leu Ile Arg Gly Gly Ala Ala Glu Gln Ser Gly Leu Ile Gln Ala
        35                  40                  45

Gly Asp Ile Ile Leu Ala Val Asn Asp Arg Pro Leu Val Asp Leu Ser
    50                  55                  60

Tyr Asp Ser Ala Leu Glu Val Leu Arg Gly Ile Ala Ser Glu Thr His
65                  70                  75                  80

Val Val Leu Ile Leu Arg Gly Pro
                85

<210> SEQ ID NO 8

```
<211> LENGTH: 88
<212> TYPE: PRT
<213> ORGANISM: artificial
<220> FEATURE:
<223> OTHER INFORMATION: inaD-3

<400> SEQUENCE: 8

Pro Lys Ala Arg Thr Val Gln Val Arg Lys Glu Gly Phe Leu Gly Ile
1               5                   10                  15

Met Val Ile Tyr Gly Lys His Ala Glu Val Gly Ser Gly Ile Phe Ile
            20                  25                  30

Ser Asp Leu Arg Glu Gly Ser Asn Ala Glu Leu Ala Gly Val Lys Val
        35                  40                  45

Gly Asp Met Leu Leu Ala Val Asn Gln Asp Val Thr Leu Glu Ser Asn
50                  55                  60

Tyr Asp Asp Ala Thr Gly Leu Leu Lys Arg Ala Glu Gly Val Val Thr
65                  70                  75                  80

Met Ile Leu Leu Thr Leu Lys Ser
                85

<210> SEQ ID NO 9
<211> LENGTH: 95
<212> TYPE: PRT
<213> ORGANISM: artificial
<220> FEATURE:
<223> OTHER INFORMATION: inaD-1

<400> SEQUENCE: 9

Glu Leu Ile His Met Val Thr Leu Asp Lys Thr Gly Lys Lys Ser Phe
1               5                   10                  15

Gly Ile Cys Ile Val Arg Gly Glu Val Lys Asp Ser Pro Asn Thr Lys
            20                  25                  30

Thr Thr Gly Ile Phe Ile Lys Gly Ile Val Pro Asp Ser Pro Ala His
        35                  40                  45

Leu Cys Gly Arg Leu Lys Val Gly Asp Arg Ile Leu Ser Leu Asn Gly
50                  55                  60

Lys Asp Val Arg Asn Ser Thr Glu Gln Ala Val Ile Asp Leu Ile Lys
65                  70                  75                  80

Glu Ala Asp Phe Lys Ile Glu Leu Glu Ile Gln Thr Phe Asp Lys
                85                  90                  95

<210> SEQ ID NO 10
<211> LENGTH: 86
<212> TYPE: PRT
<213> ORGANISM: artificial
<220> FEATURE:
<223> OTHER INFORMATION: inaD-5

<400> SEQUENCE: 10

Leu Glu Lys Phe Asn Val Asp Leu Met Lys Lys Ala Gly Lys Glu Leu
1               5                   10                  15

Gly Leu Ser Leu Ser Pro Asn Glu Ile Gly Cys Thr Ile Ala Asp Leu
            20                  25                  30

Ile Gln Gly Gln Tyr Pro Glu Ile Asp Ser Lys Leu Gln Arg Gly Asp
        35                  40                  45

Ile Ile Thr Lys Phe Asn Gly Asp Ala Leu Glu Gly Leu Pro Phe Gln
50                  55                  60

Val Cys Tyr Ala Leu Phe Lys Gly Ala Asn Gly Lys Val Ser Met Glu
65                  70                  75                  80
```

-continued

Val Thr Arg Pro Lys Pro
            85

<210> SEQ ID NO 11
<211> LENGTH: 89
<212> TYPE: PRT
<213> ORGANISM: artificial
<220> FEATURE:
<223> OTHER INFORMATION: inaD-2

<400> SEQUENCE: 11

Lys Asp Leu Arg Arg Ile Glu Val Gln Arg Asp Ala Ser Lys Pro Leu
1               5                   10                  15

Gly Leu Ala Leu Ala Gly His Lys Asp Arg Gln Lys Met Ala Cys Phe
            20                  25                  30

Val Ala Gly Val Asp Pro Asn Gly Ala Leu Gly Ser Val Asp Ile Lys
        35                  40                  45

Pro Gly Asp Glu Ile Val Glu Val Asn Gly Asn Val Leu Lys Asn Arg
    50                  55                  60

Cys His Leu Asn Ala Ser Ala Val Phe Lys Ser Val Asp Gly Asp Lys
65                  70                  75                  80

Leu Val Met Ile Thr Ser Arg Arg Lys
                85

<210> SEQ ID NO 12
<211> LENGTH: 80
<212> TYPE: PRT
<213> ORGANISM: artificial
<220> FEATURE:
<223> OTHER INFORMATION: inaD-4

<400> SEQUENCE: 12

Pro Met Gly Val Ile Val Cys Gly Gly Lys Asn Asn His Val Thr Thr
1               5                   10                  15

Gly Cys Val Ile Thr His Val Tyr Pro Glu Gly Gln Val Ala Ala Asp
            20                  25                  30

Lys Arg Leu Lys Ile Phe Asp His Ile Cys Asp Ile Asn Gly Thr Pro
        35                  40                  45

Ile His Val Gly Ser Met Thr Thr Leu Lys Val His Gln Leu Phe His
    50                  55                  60

Thr Thr Tyr Glu Lys Ala Val Thr Leu Thr Val Phe Arg Ala Asp Pro
65                  70                  75                  80

<210> SEQ ID NO 13
<211> LENGTH: 5
<212> TYPE: PRT
<213> ORGANISM: artificial
<220> FEATURE:
<223> OTHER INFORMATION: import locolization sequence targeting nucleus

<400> SEQUENCE: 13

Lys Lys Lys Arg Lys
1               5

<210> SEQ ID NO 14
<211> LENGTH: 26
<212> TYPE: PRT
<213> ORGANISM: artificial
<220> FEATURE:
<223> OTHER INFORMATION: import locolization sequence targeting
      mitochondrion

<400> SEQUENCE: 14

```
-continued

Met Leu Arg Thr Ser Ser Leu Phe Thr Arg Arg Val Gln Pro Ser Leu
1               5                   10                  15

Phe Arg Asn Ile Leu Arg Leu Gln Ser Thr
            20                  25

<210> SEQ ID NO 15
<211> LENGTH: 4
<212> TYPE: PRT
<213> ORGANISM: artificial
<220> FEATURE:
<223> OTHER INFORMATION: import locolization sequence targeting
      endoplasmic reticulum

<400> SEQUENCE: 15

Lys Asp Glu Leu
1

<210> SEQ ID NO 16
<211> LENGTH: 4
<212> TYPE: PRT
<213> ORGANISM: artificial
<220> FEATURE:
<223> OTHER INFORMATION: insertion into plasma membrane
<221> NAME/KEY: VARIANT
<222> LOCATION: (1)..(4)
<223> OTHER INFORMATION: x = any amino acid

<400> SEQUENCE: 16

Cys Cys Xaa Xaa
1
```

COMPOSITIONS AND METHODS FOR IDENTIFYING MODULATORS OF TRANSDUCISOMES, A NEW CLASS OF THERAPEUTIC TARGETS

This application claim the benefit of Provisional application Ser. No. 60/052,588, filed Jul. 15, 1997.

FIELD OF THE INVENTION

The invention relates to compositions and methods for identifying modulators of signal transduction in cells, particularly signal transduction related to cell surface receptors and ion channels.

BACKGROUND

Many physiological signals (e.g., sensory, hormonal and neurotransmitter signals) are transduced from extacellular to intracellular environments by cell surface receptors. For example, G-protein coupled receptors (GPCRs) (for a review, see Neer, 1995, Cell 80:249–257), tyrosine kinase receptors and tyrosine phosphatase receptors are involved in signal transduction.

As an example, GPCRs mediate signal transduction across a cell membrane upon the binding of a ligand to an extracellular portion of a GPCR. The intracellular portion of a GPCR interacts with a G-protein to modulate signal transduction from outside to inside a cell. A GPCR is therefore said to be "coupled" to a G-protein. G-proteins are composed of three polypeptide subunits: an α subunit, which binds and hydolyzes GTP, and a dimeric βγ subunit. In the basal, inactive state, the G-protein exists as a heterotrimer of the α and βγ subunits. When the G-protein is inactive, guanosine diphosphate (GDP) is associated with the α subunit of the G-protein. When a GPCR is bound and activated by a ligand, the GPCR binds to the G-protein heterotrimer and decreases the affinity of the Gα subunit for GDP. In its active state, the G submit exchanges GDP for guanine triphosphate (GTP) and active Gα subunit disassociates from both the receptor and the dimeric βγ subunit. The disassociated, active Gα subunit transduces signals to effectors that are "downstream" in the G-protein signaling pathway within the cell. Eventually, the G-protein's endogenous GTPase activity returns active G subunit to its inactive state, in which it is associated with GDP and the dimeric βγ subunit.

Currently available assays of signal transduction are often hampered by low or non-specific signals. Receptor activation pathways can cross talk, leading to a loss in signal specificity. In addition, some receptors when heterologoously expressed may not function in the normal fashion due to the absence of protein(s) integral to signal transduction function. Additionally, assay tools for monitoring protein-protein interactions of signal transduction are few and cumbersome, such as antibody labeling and not well suited for high throughput screening.

Consequently, the inventors provide new methods and assays components for biochemical and cell-based assays using a newly, functionally identified class of therapeutic target, transducisome proteins. Transducisome proteins as described further herein, assembly and organize many types of signal transduction proteins using PDZ domains to permit or enhance signal transduction.

SUMMARY OF THE INVENTION

Cells respond to a wide variety of external signals mediated by cell surface receptors that transduce extracellular stimuli into an intracellular response. Although receptors that recognize different ligands are known to interact with the same intracellular signaling molecules, the specificity of signaling, often essential to a cell's physiological role, is maintained. How is this specificity maintained, or rather, how is signal cross talk avoided? One solution involves organizing different signaling cascades into physically and functionally distinct signaling units. Such assemblies can permit or enhance signal response time, specificity and selectivity while minimizing cross talk. Until the advent of present invention, know little was known about the architectural organization of the corresponding signaling machinery or how it can be used to discover useful modulators of signal transduction.

The invention provides cells and methods for identifying modulators of signal transduction based, in part, on transducisome proteins that coordinate and assemble many types of signal transduction proteins. Transducisomes can either permit or enhance signal transduction. By including transducisome proteins in the assays, as described herein, modulators of signal transduction can be identified. "Transducisome" refers to a PDZ domain containing protein that binds at least one signal transduction protein or a PDZ domain containing protein with at least one signal transduction protein bound to it (see FIG. 1A-C). Other types of transducisomes are described herein.

The invention includes methods for identifying modulators of signal transduction comprising contacting a transducisome in a biochemical assay, cell assay or animal assay, with a test chemical and detecting a change in signal transduction. As described herein the invention includes animals (e.g., mice and flies), cells (e.g., mammalian and insect), with transducisomes, modified transducisomes and defective transducisomes to use in assays of signal transduction. The invention also includes proteins (as well as polynucleotides encoding the same) corresponding to transducisomes, modified transducisomes or defective transducisomes to use in assays of signal transduction.

The invention also includes a screening assay system for detecting protein-protein interactions. This screening assay system comprises a recombinant protein comprising at least one PDZ domain; a PDZ binding protein; and at least one test chemical. The recombinant protein or the PDZ binding protein or both have a label to facilitate the detection of specific binding. Preferably, the recombinant protein has a donor and the PDZ binding protein has a quencher, wherein the donor and quencher are energy transfer partners, as described herein. The PDZ binding protein can be selected from the group of a kinase, a phosphatase, a GPCR, a tyrosine kinase receptor, a tyrosine phosphatase receptor, an ion channel, a G-protein, a phospholipase and calcium binding protein. More preferably, the energy transfer partners are a modified GFP FRET partner pair.

BRIEF DESCRIPTION OF THE DRAWINGS

FIG. 2A shows a diagram of INAD protein with the locations of and size of each PDZ domain highlighted. Also shown are the relative locations of the three inaD mutations related to photoreceptor activation.

FIG. 2B shows an amino acid alignment of PDZ domains from mammalian PSD-95[9], nNOS[23], Drosophila dlg[8] and inaD[36]. Black boxes indicate amino acid identities and gray boxes show conservative substitutions. Stars above the sequence indicate residues implicated in substrate binding[27]. The circled residues refer to the site of point mutation in the three Drosophila inaD alleles (see text for details) (SEQ ID NOS:3–12).

FIG. 3B also shows that the third PDZ domain of INAD is specific for TRP[37], while the fourth domain specifically interacts with eye-PKC and the fifth domain specifically interacts with $PLC_\beta$. Overexpression of each of the individual PDZ domains from INAD as GST-PDZ fusions produce highly preferred interactions in biochemical assays.

DEFINITIONS

Figure 1A:
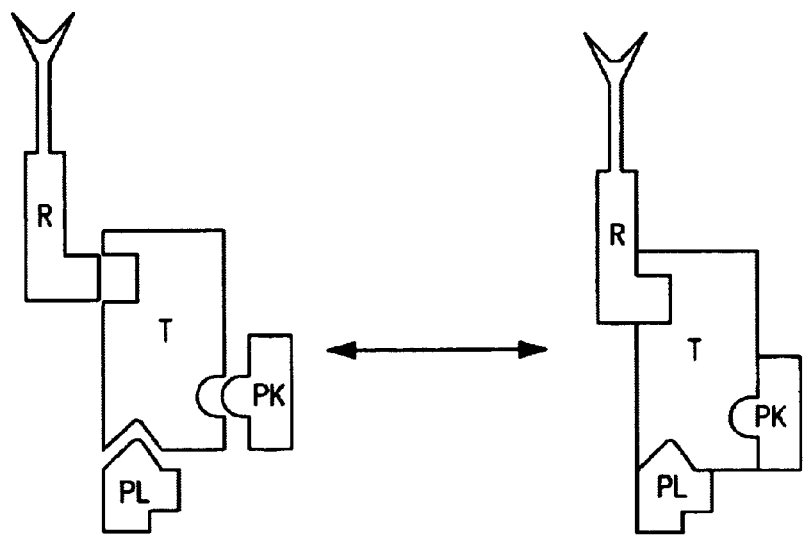
FIG. 1A shows an exemplary transducisome in the uncomplexed and complexed state. A transducisome protein "T" has three different PDZ domains that bind different signal transduction proteins such as a phospholipase ("PL"), a phosphokinase ("PK") and a cell surface receptor ("R"). The interlocking regions on the transducisome protein illustrate PDZ domains that bind signal transduction proteins. The interlocking region on each signal transduction protein illustrates an amino acid region that binds a PDZ domain on the transducisome protein.
Figure 1B:
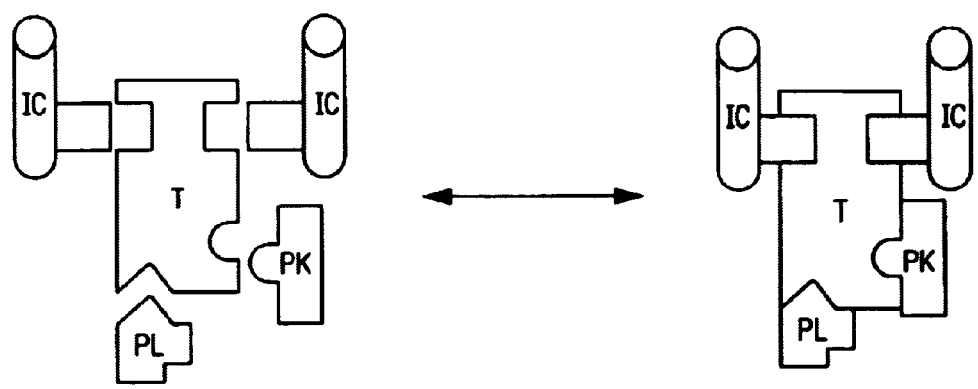
FIG. 1B shows an exemplary transducisome in the uncomplexed and complexed state. A transducisome protein "T" has three different PDZ domains that bind signal transduction proteins such as a phospholipase ("PL"), a phosphokinase ("PK") and two ion channels of the same type ("IC"). The interlocking regions on the transducisome protein illustrate PDZ domains that bind signal transduction proteins. The interlocking region on each signal transduction protein illustrates an amino acid region that binds a PDZ domain on the transducisome protein.

Unless defined otherwise, all technical and scientific terms used herein have the same meaning as commonly understood by one of ordinary skill in the art to which this invention belongs. Generally, the nomenclature used herein and the laboratory procedures in spectroscopy, drug discovery, cell culture, and molecular genetics, described below are those well known and commonly employed in the art. Standard techniques are typically used for preparation of signal detection, recombinant nucleic acid methods, polynucleotide synthesis, and microbial culture and transformation (e.g., electroporation, and lipofection). The techniques and procedures are generally performed according to conventional methods in the art and various general references (see generally, Sambrook et al. Molecular Cloning: A Laboratory Manual, 2d ed. (1989) Cold Spring Harbor Laboratory Press, Cold Spring Harbor, N.Y., and Lakowicz, J. R. Principles of Fluorescence Spectroscopy, New York: Plenum Press (1983) for fluorescence techniques, which are incorporated herein by reference) which are provided throughout this document. Standard techniques are used for chemical syntheses, chemical analyses, and biological assays. As employed throughout the disclosure, the following terms, unless otherwise indicated, shall be understood to have the following meanings:

"Fluorescent donor moiety" refers to the radical of a fluorogenic compound, which can absorb energy and is capable of transferring the energy to another fluorogenic molecule or part of a compound. Suitable donor fluorogenic molecules include, but are not limited to, coumarins and related dyes xanthene dyes such as fluoresceins, rhodols, and rhodamines, resorufins, cyanine dyes, bimanes, acridines, isoindoles, dansyl dyes, aminophthalic hydrazides such as luminol and isoluminol derivatives, aminophthalimides, aminonaphthalimides, aminobenzofurans, aminoquinolines, dicyanohydroquinones, and europium and terbium complexes and related compounds.

"Quencher" refers to a chromophoric molecule or part of a compound, which is capable of reducing the emission from a fluorescent donor when attached to the donor. Quenching may occur by any of several mechanisms including fluorescence resonance energy transfer, photoinduced electron transfer, paramagnetic enhancement of intersystem crossing, Dexter exchange coupling, and excitation coupling such as the formation of dark complexes.

"Acceptor" refers to a quencher that operates via fluorescence resonance energy transfer. Many acceptors can re-emit the transferred as energy as fluorescence. Examples include coumarins and related fluorophores, xanthenes such as fluoresceins, rhodols, and rhodamines, resorufins, cyanines, difluoroboradiazaindacenes, and phthalocyanines. Other chemical classes of acceptors generally do not re-emit the transferred energy. Examples include indigos, benzoquinones, anthraquinones, azo compounds, nitro compounds, indoanilines, di- and triphenylmethanes.

"Binding pair" refers to two moieties (e.g. chemical or biochemical) that have an affinity for one another. Examples of binding pairs include antigen/antibodies, lectin/avidin, target polynucleotide/probe oligonucleotide, antibody/anti-antibody, receptor/ligand, enzyme/ligand and the like. "One member of a binding pair" refers to one moiety of the pair, such as an antigen or ligand.

"Dye" refers to a molecule or part of a compound that absorbs specific frequencies of light, including but not limited to ultraviolet light. The terms "dye" and "chromophore" are synonymous.

"Fluorophore" refers to a chromophore that fluoresces.

"Membrane-permeant derivative" refers a chemical derivative of a compound that has enhanced membrane permeability compared to an underivativized compound. Examples include ester, ether and carbamate derivatives. These derivatives are made better able to cross cell membranes, i.e. membrane permeant, because hydrophilic groups are masked to provide more hydrophobic derivatives. Also, masking groups are designed to be cleaved from a precursor (e.g., fluorogenic substrate precursor) within the cell to generate the derived substrate intracellularly. Because the substrate is more hydrophilic than the membrane permeant derivative it is now trapped within the cells.

"Isolated polynucleotide" refers a polynucleotide of genomic, cDNA, or synthetic origin or some combination there of, which by virtue of its origin the "isolated polynucleotide" (1) is not associated with the cell in which the "isolated polynucleotide" is found in nature, or (2) is operably linked to a polynucleotide which it is not linked to in nature.

"Isolated protein" refers a protein, usually of cDNA, recombinant RNA, or synthetic origin or some combination thereof, which by virtue of its origin the "isolated protein" (1) is not associated with proteins that it is normally found with in nature, (2) is isolated from the cell in which it normally occurs, (3) is isolated free of other proteins from the same cellular source, e.g. free of human proteins, (4) is expressed by a cell from a different species, or (5) does not occur in nature. "Isolated naturally occurring protein" refers to a protein which by virtue of its origin the "isolated naturally occurring protein" (1) is not associated with proteins that it is normally found with in nature, or (2) is isolated from the cell in which it normally occurs or (3) is isolated free of other proteins from the same cellular source, e.g. free of human proteins.

"Polypeptide" as used herein as a generic term to refer to native protein, fragments, or analogs of a polypeptide sequence. Hence, native protein, fragments, and analogs are species of the polypeptide genus. Preferred transducisome polypeptides, include those with the polypeptide sequence represented in the SEQUENCE ID LISTING (as well as human homologs hereof) and any other protein having activity similar to such transducisome proteins as measured by one or more of the assays described herein. SEQ. ID NO.: 1 is a transducisome protein (fly) amino acid sequence and SEQ. ID NO. 2 is a transducisome protein (fly) nucleotide sequence. Transducisome polypeptides or proteins can include any protein having sufficient activity for detection in the assays described herein.

"Naturally-occurring" as used herein, as applied to an object, refers to the fact that an object can be found in nature. For example, a polypeptide or polynucleotide sequence that is present in an organism (including viruses) that can be isolated from a source in nature and which has not been intentionally modified by man in the laboratory is naturally-occurring.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences, such as when the appropriate molecules (e.g., inducers and polymerases) are bound to the control or regulatory sequence(s).

"Control sequence" refers to polynucleotide sequences which are necessary to effect the expression of coding and noncoding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, components whose presence can influence expression, and can also include additional components whose presence is advantageous, for example, leader sequences and fusion partner sequences.

"Polynucleotide" refers to a polymeric form of nucleotides of at least 10 bases in length, either ribonucleotides or deoxynucleotides or a modified form of either type of nucleotide. The term includes single and double stranded forms of DNA.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, 1972, Volume 5, National Biomedical Research Foundation, pp. 101–110, and Supplement 2 to this volume, pp. 1–10. The two sequences or parts thereof are more preferably homologous if their amino acids are greater than or equal to 30% identical when optimally aligned using the ALIGN program.

"Corresponds to" refers to a sequence that is homologous (i.e., is identical, not strictly evolutionarily related) to all or a portion of a reference sequence.

The following terms are used to describe the sequence relationships between two or more proteins: "reference sequence," "comparison window," "sequence identity," "percentage of sequence identity," and "substantial identity." A "reference sequence" is a defined sequence used as a basis for a sequence comparison; a reference sequence may be a subset of a larger sequence, for example, as a segment of a full-length protein given in a sequence listing such as a SEQ. ID NO. 1, or may comprise a complete protein sequence. Generally, a reference sequence is at least 400 nucleotides in length, frequently at least 600 nucleotides in length, and often at least 800 nucleotides in length (or the protein equivalent). Since two proteins may each (1) comprise a sequence (i.e., a portion of the complete protein sequence) that is similar between the two proteins, and (2) may further comprise a sequence that is divergent between the two proteins, sequence comparisons between two (or more) proteins are typically performed by comparing sequences of the two proteins over a "comparison window" to identify and compare local regions of sequence similarity. A "comparison window," as used herein, refers to a conceptual segment of at least 20 contiguous amino acid positions wherein a protein sequence may be compared to a reference sequence of at least 20 contiguous amino acids and wherein the portion of the protein sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two protein sequences are identical (i.e., on a nucleotide-by-nucleotide basis) over the window of comparison. The term "percentage of sequence identity" is calculated by comparing two optimally aligned sequences over the window of comparison, determining the number of positions at which the identical amino acids occurs in both sequences to yield the number of matched positions, dividing the number of matched positions by the total number of positions in the window of comparison (i.e., the window size), and multiplying the result by 100 to yield the percentage of sequence identity.

As applied to proteins, the term "substantial identity" means that two protein sequences, when optimally aligned, such as by the programs GAP or BESTFIT using default gap weights, typically share at least 70 percent sequence identity, preferably at least 80 percent sequence identity, more preferably at least 90 percent sequence identity, and most preferably at least 95 percent sequence identity. Preferably, residue positions, which are not identical, differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are valine-leucine-isoleucine, phenylalanine-tyrosine, lysine-arginine, alanine-valine, glutamic-aspartic, and asparagine-glutamine.

"Transducisome protein" refers to a protein with the transducisome protein activity of one of the transducisome proteins of the SEQ. ID listing or another PDZ domain containing protein that binds signal transduction proteins. Preferably, the transducisome protein can functionally bind at least one signal transduction protein. Examples of transducisome proteins include INAD, GRIP and other recently identified multi-PDZ domain proteins. Examples of signal transduction proteins include GPCRs, tyrosine kinase receptors, tyrosine phosphatase receptors, ion channels, phospholipases, adenylate cyclases, kinases and G-proteins. Transducisome protein activity can be measured with endogenously or heterologously expressed transducisome proteins and signal transduction proteins using the assays described herein. Preferably, a transducisome protein can functionally bind to at least two different types of signal transduction proteins, more preferably, a transducisome protein can functionally bind to at least three different types of signal transduction proteins. Transducisome proteins permit enhanced signal transduction by signal transduction proteins compared to signal transducton by signal transduction proteins not functionally bound to a transducisome. Transducisome protein activity includes functional binding of a signal transduction protein to a transducisome protein, alteration of signal transduction protein activity when the signal transduction protein is complexed to the transducisome protein (e.g., a increase or decrease in activity or a change in signal transduction protein specificity) and any other activity related to signal transduction induced by a transducisome protein. Mammalian transducisome proteins for use with mammalian signal transduction proteins are preferred, particularly human transducisome proteins.

"Modulation" refers to the capacity to either enhance or inhibit a functional property of biological activity or process (e.g., enzyme activity or receptor binding); such enhancement or inhibition may be contingent on the occurrence of a specific event, such as activation of a signal transduction pathway, and/or may be manifest only in particular cell types.

The term "modulator" refers to a chemical (naturally occurring or non-naturally occurring), such as a synthetic molecule (e.g., nucleic acid, protein, non-peptide, or organic molecule), or an extract made from biological materials such as bacteria, plants, fungi, or animal (particularly mammalian) cells or tissues. Modulators are evaluated for potential activity as inhibitors or activators (directly or indirectly) of a biological process or processes (e.g., agonist, partial antagonist, partial agonist, inverse agonist, antagonist, antineoplastic agents, cytotoxic agents, inhibitors of neoplastic transformation or cell proliferation, cell proliferation-promoting agents, and the like) by inclusion in screening assays described herein. The activity of a modulator may be known, unknown or partially known.

"Sequence homology" refers to the proportion of base matches between two nucleic acid sequences or the proportion amino acid matches between two amino acid sequences. When sequence homology is expressed as a percentage, e.g., 50%, the percentage denotes the proportion of matches over the length of sequence from a desired sequence (e.g., SEQ. ID NO. 1) that is compared to some other sequence. Gaps (in either of the two sequences) are permitted to maximize matching; gap lengths of 15 bases or less are usually used, 6 bases or less are preferred with 2 bases or less more preferred.

The term "test chemical" refers to a chemical to be tested by one or more screening method(s) of the invention as a putative modulator. A test chemical is usually not known to bind to the target of interest. The term "control test chemical" refers to a chemical known to bind to the target (e.g., a known agonist, antagonist, partial agonist or inverse agonist). The term "test chemical" does not include a chemical added as a control condition that alters the function of the target to determine signal specificity in an assay. Such control chemicals or conditions include chemicals that 1) non-specifically or substantially disrupt protein structure (e.g., denaturing agents (e.g., urea or guandium), charotropic agents, sulfhydryl reagents (e.g., dithiotritol and β-mercaptoethanol), and proteases), 2) generally inhibit cell metabolism (e.g., mitochondrial uncouplers) and 3) non-specifically disrupt electrostatic or hydrophobic interactions of a protein (e.g., high salt concentrations, or detergents at concentrations sufficient to non-specifically disrupt hydrophobic interactions). The term "test chemical" also does not include chemicals known to be unsuitable for a therapeutic use for a particular indication due to toxicity of the subject. Usually, various predetermined concentrations test chemicals are used for screening such as 0.01 µM, 0.1 µM, 1.0 µM, and 10.0 µM.

The term "target" refers to a biochemical entity involved a biological process. Targets are typically proteins that play a useful role in the physiology or biology of an organism. A therapeutic chemical binds to target to alter or modulate its function. As used herein targets can include cell surface receptors, G-proteins, kinases, ion channels, phopholipases and other proteins mentioned herein.

The terms "label" or "labeled" refers to incorporation of a detectable marker, e.g., by the incorporation of a radio labeled amino acid or attachment to a polypeptide of biotinyl moieties that can be detected by marked avidin (e.g., streptavidin containing a fluorescent marker or enzymatic activity that can be detected by optical, or colorimetric methods). Various methods of labeling polypeptides and glycoproteins are known in the art and may be used. Examples of labels for polypeptides include, but are not limited to, the following: radioisotopes (e.g., $^3$H, $^{14}$C, $^{35}$S, $^{125}$I, $^{131}$I), fluorescent labels (e.g., FITC, rhodamine, and lanthanide phosphors), enzymatic labels or reporter genes (e.g., horseradish peroxidase, β-galactosidase, β-latamase, luciferase, alkaline phosphatase), chemiluminescent groups, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

"Fluorescent label" refers to incorporation of a detectable fluorescent marker, e.g., by incorporation of a fluorescent moiety to a chemical entity that binds to a target or attachment to a polypeptide of secondary attachment molecules, such as biotinyl moieties that can be detected by avidin (e.g., streptavidin containing a fluorescent label or enzymatic activity that can be detected by fluorescence detection methods). Examples of fluorescent labels for polypeptides include, but are not limited to dyes (e.g., FITC and rhodamine), intrinsically fluorescent proteins, and lanthanide phosphors. In some embodiments, labels are attached by spacer arms of various lengths to reduce potential steric hindrance and in some embodiments to facilitate energy transfer.

"Reporter gene" refers to a nucleotide sequence encoding a protein that is readily detectable either by its presence or activity, including, but not limited to, luciferase, fluorescent protein (e.g., green fluorescent protein), chloramphenicol acetyl transferase, β-galactosidase, secreted placental alkaline phosphatase, β-lactamase, human growth hormone, and other secreted enzyme reporters. Generally, reporter genes encode a polypeptide not otherwise produced by the host cell, which is detectable by analysis of the cell(s), e.g., by the direct fluorometric, radioisotopic or spectrophotometric analysis of the cell(s) and preferably without the need to kill the cells for signal analysis. Preferably, the gene encodes an enzyme, which produces a change in fluorometric properties of the host cell, which is detectable by qualitative, quantitative or semi-quantitative function of transcriptional activation. Exemplary enzymes include esterases, β-lactamase, phosphatases, proteases (tissue plasminogen activator or urokinase) and other enzymes whose function can be detected by appropriate chromogenic or fluorogenic substrates known to those skilled in the art or developed in the future. "Signal transduction" refers to the coupling of an extracellular signal to an intracellular response.

"Signal transduction detection system" refers to a system for detecting signal transduction across a cell membrane, typically a cell plasma membrane. Such systems typically detect at least one activity or physical property directly or indirectly associated with signal transduction. For example, an activity or physical property directly associated with signal transduction is the activity or physical property of either the receptor (e.g., GPCR), or a coupling protein (e.g., a Gα protein). Signal transduction detection systems for monitoring an activity or physical property directly associated with signal transduction, include GTPase activity, ion channel activity and conformational changes. An activity or physical property indirectly associated with signal transduction is the activity or physical property produced by a molecule other than by either the receptor (e.g., GPCRs, tyrosine kinase receptors, or tyrosine phoshphatase receptors), ion channel or a coupling protein (e.g., a Gα protein) associated with a receptor (e.g., GPCRs, tyrosine kinase receptors, or tyrosine phoshphatase receptors), or a coupling protein (e.g., a Gα protein). Such indirect activities and properties include changes in intracellular levels of molecules (e.g., ions (e.g., Ca, Na or K), second messenger levels (e.g., cAMP, cGMP and inositol phosphate)), kinase activities, transcriptional activity, enzymatic activity, phospholipase activities, ion channel activities and phosphatase activities. Signal transduction assays are further described in commonly owned U.S. applications by Negulescu et al, 60/020,234, filed Jun. 21, 1996 and serial number not yet available Jun. 19, 1997. Signal transduction detection systems for monitoring an activity or physical property indirectly associated with signal transduction, include transcriptional-based assays, enzymatic assays, intracellular ion assays and second messenger assays.

"Transducisome" refers to a PDZ domain containing protein that binds at least one signal transduction protein or a PDZ domain containing protein with at least one signal transduction protein bound to it. For example, a transducisome may be an "uncomplexed transducisome" comprising only the PDZ domain containing protein. Alternatively, a transducisome may be a "complexed transducisome" comprising comprising the PDZ domain containing protein and a signal transduction protein. For instance, a complexed transducisome may contain at least two different PDZ domains bound to at least two different signal transduction protein partners that separately recognize their respective PDZ domains. Typically, a complexed transducisome can enhance signal transduction activity compared 1) signal transduction proteins that are not functionally bound to a transducisome or 2) an uncomplexed transducisome. Transducisome protein only refers to the uncomplexed transducisome.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference).

A DETAILED DESCRIPTION OF THE INVENTION

Cells respond to a wide variety of external signals mediated by cell surface receptors that transduce extracellular stimuli into an intracellular response. Receptors vary in type based on their properties, including structural similarities, signaling properties and intracellular pathways (e.g., G protein coupled receptors, tyrosine kinase receptors, and tyrosine phophatase receptors). Although receptors that recognize different ligands are known to interact with the same intracellular signaling molecules, the specificity of signaling, often essential to a cell's physiological role is maintained. How is this specificity maintained, or rather, how is signal cross talk avoided? One solution involves organizing different signaling cascades into physically and functionally distinct signaling units. Such assemblies can permit or enhance signal response time, specificity and selectivity while minimizing cross talk. Until the advent of present invention, little was known about the architectural organization of the corresponding signaling machinery or how it can be used to discover useful modulators of signal transduction.

The invention provides cells and methods for identifying modulators of signal transduction based, in part, on transducisome proteins that coordinate and assemble many types of signal transduction proteins. Transducisomes can either permit or enhance signal transduction. By including transducisome proteins in the assays, as described herein, modulators of signal transduction can be identified. "Transducisome" refers to a PDZ domain containing protein that binds at least one signal transduction protein or a PDZ domain containing protein with at least one signal transducton protein bound to it.

The invention includes methods for identifying modulators of signal transduction comprising contacting a transducisome in a biochemical assay, cell assay or animal assay, with a test chemical and detecting a change in signal transduction. As described herein the invention includes animals (e.g., mice and flies), cells (e.g., mammalian and insect), with transducisomes, modified transducisomes and defective transducisomes to use in assays of signal transduction. The invention also includes proteins (as well as polynucleotides encoding the same) corresponding to transducisomes, modified transducisomes or defective transducisomes to use in assays of signal transduction.

The Drosophila phototransduction is described herein as an example of signal transduction, as it was used by the inventors to demonstrate for the first time the function and structure of a transducisome. The phototransduction cascade is a G protein-coupled, PLC-signaling pathway that shares many features with other signaling cascades[30]. Drosophila photoreceptor neurons also show a high degree of architectural organization, with most of the molecules involved in phototransduction localized to the rhabdomeres, a specialized subcellular compartment consisting of approximately 60,000 tightly packed microvilli, 1–2 ìm in length and 50 nm wide[31]. In rhabdomeres, light activation of rhodopsin activates a Gqα, which in turn activates a $PLC_\beta$[32]. $PLC_\beta$ catalyzes the breakdown of phosphatidylinositol bisphosphate ($PIP_2$) into the two intracellular messengers inositol triphosphate ($IP_3$) and diacylglycerol (DAG), which leads to the eventual opening (and modulation) of the TRP and TRPL light-activated channels[33]. Following termination of the stimulus, calcium-dependent regulatory processes, including activation of eye-PKC, mediate deactivation of the light response[34]. InaD is one of the many loci that have been identified in genetic screens designed to dissect this signaling cascade. A single mutant allele, $InaD^{215}$, was isolated and shown to have a dominant negative phenotype on photoreceptor deactivation[35,36]. The INAD protein was shown to contain at least two PDZ domains[36], and to interact with the TRP ion channel[37]. More recently, several groups reported that INAD can be found associated with multiple components of the phototransduction cascade, including $PLC_\beta$, eye-PKC, rhodopsin and calmodulin[37–39]. These results were used to argue that INAD is a regulatory component involved in feedback regulation of the light response[39]. In surprising contrast to such previous work, the present invention shows that the INAD protein is composed of five distinct PDZ domains, and functions as the organizing scaffold for photoreceptor signaling complexes in vivo. The genetic, physiological and cell biological studies of the inventors demonstrate the presence of a multivalent adapter protein that links multiple signaling components within the same cascade, and provides a fundamental role for PDZ domains in the assembly of transduction complexes in vivo.

The advantages of spatially and temporarily restricting signal transduction proteins with transducisomes are significant. A cell can optimize, and tune, its responses to different pathways by controlling the recruitment of different signaling molecules into the different transduction complexes, thus enhancing specificity and speed, while minimizing cross talk. An example is the yeast mating response, in which the product of the sterile 5 gene functions as a scaffold protein, coordinating the recruitment of several kinases within the same signaling pathway[45–47].

The inventors used phototransduction in Drosophila as a model to study the organization of G protein-coupled transduction complexes in vivo and in vitro in the Examples. In this signaling pathway, photoreceptor neurons report activity with exquisite sensitivity and specificity. In addition, photoreceptors achieve superb temporal resolution by ensuring that the transduction machinery is reset quickly after generating a response. Phototransduction in Drosophila is the fastest known G protein-coupled cascade, taking just a few tens of milliseconds to go from light activation of rhodopsin to the generation of a receptor potential, and less than 100 ms to shut-off following termination of the stimulus[30]. The transducisome protein, INAD, coordinates the recruitment of components involved both in activation ($PLC_\beta$ and TRP), as well as in deactivation (eye-PKC)[34]. An important strategy used by photoreceptors to attain high response speed is to assemble signaling molecules into organized transducisomes. In this setting, response time would not be limited by the diffusion of different signaling components within a microvillus. This model of signal transduction, as well as other examples of drosophila biology, applies to signal transduction in humans.

A photoreceptor neuron attains high sensitivity by having an exceptionally large number of receptor molecules in its surface (~100×10$^6$ rhodopsins/cell)[48,49]. To rapidly and efficiently couple this large number of receptor molecules to the downstream transduction complexes, a diffusable coupling molecule would be required. The G protein is an ideal candidate for this function. In this model, each G protein would need only to sample a small number of receptors in the membrane (i.e. an ultra-microdomain of signaling) and report their activity to the downstream transduction complexes. The Examples show that neither rhodopsin, nor Gα are included in the INAD complexes (transducisomes) while PKC, TRP ion channel and PLCβ are part of the transducisome.

Transducisomes also contribute to the nature of unitary (i.e. single photon) responses in the eye. A quantum bump represents the coordinated activation of a few hundred light-activated ion channels in response to the activation of a single rhodopsin molecule[30]. The organization of INAD complexes into a supramolecular complex, either via PDZ-PDZ domain interactions or PDZ-cytoskeletal interactions within a microvillus, represents the structural basis of a quantum bump, insuring both reliability and coordinated signaling.

Transducisomes can be identified and selected for screens and assays described herein, by analyzing the structural basis of, and the interaction between, PDZ domains and their targets. For instance, the X-ray crystallographic structure of the third PDZ domain from the synaptic protein PSD-95, alone or in complex with its peptide ligand has been determined and can be used as a model[5,27,28]. In addition, peptide libraries can be generated to display different target sites that bind PDZ domains and show preferences for distinct PDZ domains.[40] Using such in vitro assays, PDZ domains that share structural elements and represent different PDZ domains can be easily separated to show specificity for different target proteins. The inventors have also showed this to be the case in vivo. The finding that INAD is composed primarily of PDZ domains indicates the importance of this protein motif in the organization of signaling pathways. Recently, a new protein, GRIP (glutamate receptor interacting protein), composed solely of seven PDZ domains has been identified in mammalian cells[50] and can be involved in functioning as a signaling scaffold, organizing specific transduction complexes at the synapse. Current models of PDZ-target interaction involve a binding site composed of S/TXV residues at the absolute C-terminal end of the target protein, which is a preferred region to leave unaltered in many embodiments of the invention.[5,27,29,40] In other embodiments of the invention, PDZ binding regions of targets can be located at other sites, such as located within 120 amino acid of the n-terminus of the target. For example, all three INAD targets lack such a motif (position −4 from the C-terminus in TRP, positions −122 and −507 in eye-PKC and several sites $PLC_{\beta}$, the closest at residue −26). In addition, transducisome proteins can function as modular proteins by maintaining separate binding functions in different regions. For example, INAD functions as a modular protein and is demonstrated by the fact that eliminating one target does not prevent INAD's ability to interact with the others. By using the methods described herein, it is possible to custom design transduction complexes by manipulating the number, orientation and distribution of PDZ domains in of transducisome proteins. The availability of mutant transducisomes, such as null inaD mutant, makes assays based on such compositions now possible.

Many signal transduction proteins can be recruited and assembled into larger complexes, transducisomes, by protein-protein interaction domains. Proteins interacting with, or containing, PDZ domains[8-12], are often localized at the plasma membrane[13-15]. Thus, PDZ domains provide a framework for recruiting target molecules into membrane-bound macromolecular complexes. Recently, the PDZ-domain protein PSD-95 has been shown to mediate the clustering of both NMDA receptors[12,16-18] and $K^+$ channels[19-22]. In addition, members of the PSD-95/93 family form synaptic complexes[16,23-25], and a PDZ domain in FAP1 binds to the FAS membrane receptor[26]. In other embodiments, PDZ-PDZ interactions can mediate of protein-protein interactions[26]. To date, PDZ domains have been found in more than 50 proteins, including many involved in cell signaling and can be used as a source of signal transduction proteins.[27-29]

One aspect of the invention includes a method of identifying modulators of signal transduction. The method comprises contacting a first cell with a test chemical, wherein the first cell comprises at least one signal transduction protein and a polynucleotide encoding a transducisome protein. The traducisome protein functionally binds to the signal transduction protein to permit or enhance signal transduction. The method can include activating signal transduction in the first cell either with the test chemical or with another chemical. The method includes the step of detecting signal transduction from the first cell with a signal transduction detection system. Different types of cells are described herein and mammalian cells, particularly human cells, are preferred. Signals from the first cell can be compared with signals from a second cell assayed under different conditions, for instance under control conditions.

For example, the method includes contacting a second cell with the test chemical, wherein the second cell comprises the signal transduction protein and a polynucleotide encoding a defective transducisome protein. The defective transducisome protein fails to functionally bind at least one signal transduction protein to permit or enhance signal transduction. Alternatively, second cell may be used that fails to express the transducisome protein to permit the transducisome protein to functionally bind to at least one signal transduction protein to permit or enhance signal transduction. The method can include the step of activating signal transduction in the second cell with a test chemical or another chemical and detecting signal transduction from the second cell with a signal transduction detection system. The method includes the step of comparing signal transduction from the first cell with signal transduction from the second cell. Often the second cell is the same type of cell as the first cell. The second cell can also comprise an amino acid mutation in a PDZ domain of the defective transducisome protein that prevents functional binding of a signal transduction protein, as described herein.

Another aspect of the invention includes a method of identifying modulators of signal transduction by overexpressing the transducisome protein to enhance or permit signal transducton. The method comprises contacting a cell with a test chemical, wherein the first cell comprises at least one signal transduction protein and a polynucleotide encoding a transducisome protein, the polynucleotide permits increased expression of the transducisome protein and the transducisome protein functionally binds to the signal transduction protein to permit or enhance signal transduction compared to the absence of increased expression of the transducisome protein. The method includes optionally activating the signal transduction with a signal that increases or activates the signal transduction in the cell, and detecting signal transduction from the first cell with a signal transduction detection system.

The method can also include contacting a second cell with the test chemical. Wherein the second cell comprises the signal transduction protein and a polynucleotide encoding a defective transducisome protein. The defective transducisome protein fails to functionally bind the signal transduction protein to permit or enhance signal transduction or the second cells fails to express the transducisome protein to permit the transducisome protein to functionally bind to the signal transduction protein to permit or enhance signal transduction. Signal transduction from the second cell is detected with a signal transduction detection system, and compared to signal transduction from the first cell. Alternatively, the method can include contacting a second cell with the test chemical, wherein the second cell lacks the signal transduction protein to permit the transducisome protein to functionally bind to the signal transduction protein to permit or enhance signal transduction.

The signal for signal transduction can be any signal compatible with the assay being used. The signal may be a test chemical itself or a known activator of signal transduction. The activating step can include activating signal transduction with a signal selected from the group consisting of a chemical signal found in blood, a chemical signal found in a synaptic cleft, a chemical signal found in interstitial fluid, light or a chemical signal found in air or other signals known the art or developed in the future.

In preferred embodiments described herein, the signal transduction protein is heterologously expressed and is selected from the group consisting of a kinase, a phosphatase, a GPCR, a tyrosine kinase receptor, a tyrosine phosphatase receptor, an ion channel, a G-protein, a phospholipase and a calcium binding protein.

Another aspect of the invention, is a method of identifying modulators of a cell surface receptor using transducisome proteins. The method comprises contacting a cell with a test chemical, wherein the cell comprises at least one cell surface receptor and a polynucleotide encoding a transducisome protein. The polynucleotide permits increased expression of the transducisome protein and the transducisome protein functionally binds to the cell surface receptor to permit or enhance signal transduction compared to the absence of increased expression of the transducisome protein. Signals can be detected associated with the cell surface receptor in the presence and absence of the test chemical or known ligand of the receptor. Various cells and receptors described herein or known in the art can be used.

In regard to receptors, the invention also provides a method of identifying modulators of a GPCR. The method includes contacting a cell with a test chemical, wherein the cell comprises a polynucleotide encoding a GPCR comprising one or more regions that bind a PDZ domain(s) and a polynucleotide encoding a heterologous protein comprising a PDZ domain that binds the GPCR. The method includes detecting a signal associated with the activity the GPCR. Various methods may be employed with the present invention concerning the screening of GPCRs, including the use of response elements and promiscuous G proteins, as described in commonly owned U.S. applications by Negulescu et al, 60/020,234, filed Jun. 21, 1996 and serial number not yet available, filed Jun. 19, 1997, herein incorporated by reference.

Such embodiments, as well as other embodiments described herein, are particularly well suited for identifying modulators to prevent or reduce the association of specific signal transduction proteins with a transducisome. Thus, such modulators alter signal transduction by reducing the amount of complexed transducisomes. Such modulations can often reduce signal transducton without completely eliminating signal transduction, which can enable to the cell to perform a basal level of activity. This can be an advantage compared to a antagonist that completely inactivates the receptor.

The invention also includes a method of identifying modulators of an ion channel using transducisome proteins. The method comprises contacting a cell with a test chemical, wherein the cell comprises at least one ion channel and a polynucleotide encoding a transducisome protein, the polynucleotide permits increased expression of the transducisome protein. The transducisome protein functionally binds to the ion channel to permit or enhance signal transducton compared to the absence of increased expression of the transducisome protein. The method includes detecting a signal associated with the activity the ion channel.

Alternatively, the invention provides another a method of identifying modulators of an ion channel. The method comprises contacting a cell with a test chemical, wherein the cell comprises a polynucleotide encoding an ion channel comprising one or more regions that bind PDZ domains and a polynucleotide encoding a heterologous protein comprising a PDZ domain that binds the ion channel. The method includes detecting a signal associated with the activity the ion channel.

Another aspect of the invention provides for a screening assay system for identifying modulators of transducisomes. The screening assay system comprises an isolated, non-naturally occurring cell comprising at least one signal transduction protein and a polynucleotide encoding a transducisome protein. The polynucleotide permits increased expression (including inducible or constitutive expression) of the transducisome protein. The transducisome protein functionally binds to the signal transduction protein to permit or enhance signal transduction compared to the absence of increased expression of the transducisome protein. The screening assay system can include a signal transduction detection system for signal transduction in the isolated, non-naturally occurring cell. The assay system can further include at least one test chemical. Often such chemicals will be tested in arrays enabling high throughput screening of at least 10,000 chemicals per day.

The invention also includes a screening assay system for detecting protein-protein interactions. This screening assay system comprises a recombinant protein comprising at least one PDZ domain, a PDZ binding protein, and at least one test chemical. The recombinant protein can be either in solution or membrane associated. The PDZ binding protein can also be either in solution or membrane associated. The test chemical is in solution. For example, the recombinant protein or the PDZ binding protein are membrane bound and the test chemical is in solution. The recombinant protein or the PDZ binding protein or both have a label to facilitate detecting specific binding. Preferably, the recombinant protein has a donor and the PDZ binding protein has a quencher, wherein the donor and quencher are energy transfer partners, as described herein. The PDZ binding protein can be selected from the group of a kinase, a phosphatase, a GPCR, a tyrosine kinase receptor, a tyrosine phosphatase receptor, an ion channel, a G-protein, a phospholipase and calcium binding protein. More preferably the energy transfer partners are a GFP or modified GFP FRET partner pair.

As described further herein, the invention provides for isolated, non-naturally occurring cells. Such cells can be used with the methods described herein and comprise 1) a heterologously expressed transducisome protein comprising one or more PDZ domains and 2) an expressed protein comprising a signal transduction protein that binds to one or more the PDZ domains.

Alternatively, the invention provides for isolated, non-naturally occurring cells, comprising: a cell capable of expressing: a) a non-naturally occurring polynucleotide comprising a coding region for a transducisome protein comprising one or more PDZ domains and b) a non-naturally occurring polynucleotide comprising a coding region for a heterologous protein comprising a signal transduction protein. The signal transduction protein can be selected from the group of a kinase, a phosphatase, a GPCR, a tyrosine kinase receptor, a tyrosine phosphatase receptor, an ion channel, a G-protein, a phospholipase and a calcium binding protein. For cell-based assays such cells will typically be contacted with a test chemical. The cell may also optionally include a signal transduction detection system.

The invention also provides for chimeric transducisome proteins. Such chimerics typically comprise at least two PDZ binding domains not found in naturally occurring proteins. Such proteins can be used to generate signal transduction systems with chimeric properties. Such system can be useful for screening for modulators of signal transduction proteins. Often such systems will have enhanced signal transduction. For example, a chimeric can include a PDZ domain that binds a phospholipase and a GPCR, where neither the phospholipase nor the GPCR normally bind to a signal PDZ containing protein. By binding to the chimeric, coupling of signal transduction will be increased between the phospholipase and the GPCR. Chmierics can comprise at least one first PDZ domain that binds a first signal transduction protein and at least one second PDZ domain binds a second signal transduction protein, wherein said chimeric transducisome protein is not a naturally occurring protein. Preferably, The chimeric transducisome protein can bind a first signal transduction protein(s) selected from the group of a kinase, a phosphatase, a GPCR, a tyrosine kinase receptor, a tyrosine phosphatase receptor, an ion channel, a G-protein, a phospholipase and a calcium binding protein. More preferably, The chimeric transducisome protein can bind second signal transduction protein is selected from the group consisting of PKC, TRP, and PLCβ.

Another aspect of the invention concerns mutant transducisome proteins that can be used in assays of transducisome function and signal transduction. Transducisome proteins with altered function can be used to determine the specificity of signals. For example, a transducisome protein that normally binds four different signal transduction proteins can be mutated to only bind signal transduction proteins A, B and C but not D. Such a transducisome protein can be used as a control for binding of signal transduction protein D. Phenotypes related to transducisomes can also be ascertained using mutant transducisome proteins.

Another aspect the invention provides for animals, such as mammals (particularly mice) or insects with mutant transducisome proteins. For example, the invention includes a fly comprising an amino acid mutation in a transducisome protein that prevents functional binding of a signal transduction protein, wherein the amino acid mutation is not a naturally occurring mutation of inaD. Preferably, the amino acid mutation results from a mutation selected from the group consisting of inaD$^2$ and inaD$^1$. Alternatively, the mutation may be in a human homolog of inaD.

In another aspect, the invention provides for an isolated cell comprising a polynucleotide encoding a transducisome protein with an amino acid mutation that prevents functional binding of a signal transduction protein, wherein the amino acid mutation is a naturally occurring mutation of inaD. Preferably, the cell is a insect cell or a mammalian cell, particularly a human cell. Preferably, the amino acid mutation results from a mutation selected from the group consisting of inaD$^2$ and inaD$^1$.

The invention provides for an isolated polynucleotide comprising a coding region for a transducisome protein with an amino acid mutation in a PDZ domain that prevents functional binding of a signal transduction protein. Typically, the amino acid mutation is not a naturally occurring mutation inaD$^{215}$. Preferably, the transducisome protein is INAD or a human homolog thereof. Preferably, the amino acid mutation results from a mutation selected from the group consisting of inaD$^2$ and inaD$^1$. The invention also provides for an isolated protein comprising a polypeptide of SEQ ID NO.: 1 with an amino acid mutation in a PDZ domain that prevents functional binding of a signal transduction protein.

The invention also includes chemicals identified by the methods described herein. For example, the invention includes chemicals identified by preventing the binding of a transducisome protein with a signal transduction protein. As a further example, the invention includes chemicals identified by the modulation of signal transduction in a either: 1) a cell comprising: a) a heterologously expressed transducisome protein comprising one or more PDZ domains and b) an expressed protein comprising a signal transduction protein that binds to one or more the PDZ domains, or 2) a cell capable of expressing: a) a non-naturally occurring polynucleotide comprising a coding region for a transducisome protein comprising one or more PDZ domains and b) a non-naturally occurring polynucleotide comprising a coding region for a heterologous protein comprising a signal transduction protein.

The invention also includes a method of treating a transducisome related disease. The method comprises administering a therapeutically effective amount of a chemical to modulate the association of a transducisome and at least one PDZ binding protein. The invention also includes a method of modulating a signal transduction in a cell, comprising contacting a cell with a chemical to modulate the association of a transducisome and at least one PDZ binding protein. The signal transduction is typically selected from the group consisting of G-protein coupled, ion channels, kinases and phospholipases. Such methods can use a therapeutic compound for treating a transducisome related disease, comprising a chemical to modulate the association of a transducisome and at least one PDZ binding protein.

Energy Transfer Compositions and Methods

In one aspect of the invention, transducisome protein interactions with signal transduction proteins can be monitored and used for identifying modulators of such interactions. The transducisome protein, a signal transduction protein, or both include a label that permits an assay for specific binding of the transducisome protein to the signal transduction protein. For example, a PDZ domain containing fragment of the transducisome protein, a fragment of a signal transduction protein that specifically binds a PDZ domain of the transducisome protein or both include a label that permits an assay for specific binding of the transducisome protein fragment to the signal transduction protein fragment. Specific binding is determined by established methods for binding assays and can include comparison to binding in the presence of control chemicals, amino acid mutations that prevent binding and other conditions as known in the art or developed in the future or described herein.

In the preferred embodiment, transducisome protein interactions with signal transduction proteins are monitored using energy transfer moieties and methods. For example, a transducisome protein can include a first energy transfer moiety (e.g., donor) and a signal transduction protein can include a second energy transfer moiety (e.g., quencher). The transducisome protein has at least one, preferably two, specific PDZ domains that separately and functionally bind at least one, preferably two, signal transduction proteins. Often the transducisome protein will recognize more than signal transduction protein, in such cases the first and second energy transfer moieties may be on signal transduction proteins to permit energy transfer between signal transduction proteins. The first energy transfer moiety and the second energy transfer moiety are suitably matched to permit to energy transfer when one is a donor and the other is an acceptor or quencher. Preferably, the energy transfer moieties are FRET (fluorescence resonance energy transfer) pairs and more preferably fluorescent proteins that are FRET pairs or partners. Although, other types of donor or acceptors can be used, as described herein and in PCT Application WO 96/30540(Tsien et al) and PCT Application WO 96/41166 (Tsien et al), particularly with labeling techniques.

Fluorescent protein FRET pairs are chosen such that the excitation spectrum of one of the moieties (the acceptor fluorescent protein moiety) overlaps with the emission spectrum of the excited protein moiety (the donor fluorescent protein moiety). The donor and acceptor fluorescent protein moieties are attached to either a transducisome protein or signal transduction protein (e.g, fusion proteins). Binding of the signal transduction protein to the transducisome protein creates a change in relative position (e.g., distance) and orientation of the donor and acceptor fluorescent protein moieties compared to the respective proteins in the unbound state (e.g., free in solution). Binding of the signal transduction protein to the transducisome protein alters the relative amounts of fluorescence, due to energy transfer from the two fluorescent protein moieties when the donor is excited by irradiation. In particular, binding of the signal transduction protein to the transducisome protein changes the ratio of the amount of light emitted by the donor and acceptor fluorescent protein moieties at a particular excitation wavelength. The ratio between the two emission wavelengths provides a measure of the binding of the signal transduction protein to the transducisome protein in the sample. Affinities related to the binding of the signal transduction protein to the transducisome protein can be readily measured, as well as reduced or increased by binding in the presence of test chemicals.

Figure 1C:
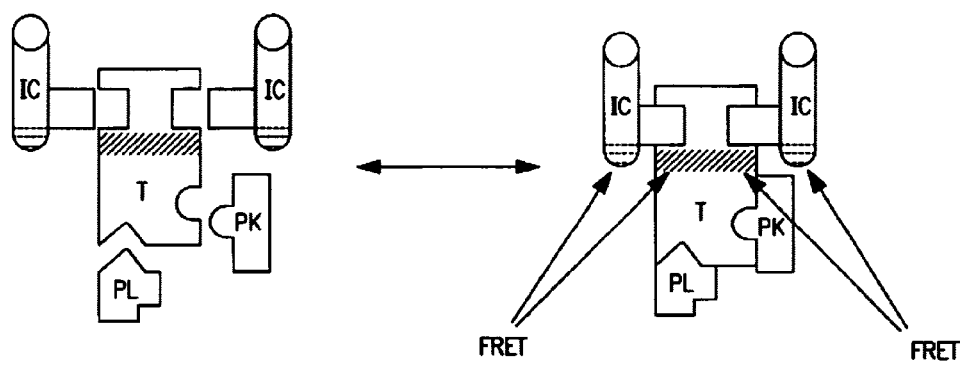
FIG. 1C shows one embodiment of the invention related monitoring protein-protein interactions in transducisomes in the uncomplexed and complexed state. The hash-marked regions represent a first energy transfer moiety for FRET. The dotted regions represent a second energy transfer moiety for FRET. FRET is substantially occurs in the complexed state between the first and second energy transfer moieties.

FIG. 1C shows, the donor fluorescent protein moiety is covalently linked to a first region (e.g., the amino terminus) of the transducisome protein, and the acceptor fluorescent protein moiety is covalently linked a first region of to the signal transduction protein (e.g., the carboxy terminus). Functional binding of the signal transduction protein to the transducisome protein decreases the distance between the donor and acceptor moieties. Both the signal transduction protein and the transducisome protein can be free in solution, membrane bound or both depending on the signal transduction system. Alternatively, the donor and acceptor moieties can move farther apart upon disassociation. A linker moiety can be added between the fluorescent protein and the transducisome protein or the signal transduction protein to enhance energy transfer. Typically, the linker moiety is flexible enough to permit binding of the signal transduction protein to the transducisome protein and allow closer association of the fluorescent moieties to facilitate a form of pseudodimerization. The fluorescent moieties themselves can be selected from dimerizing proteins to enhance energy transfer. Linking moieties are described, for example, in Huston, J. S., et al., *PNAS* 85:5879–5883 (1988), Whitlow, M., et al., *Protein Engineering* 6:989–995 (1993), and Newton, D. L., et al., *Biochemistry* 35:545–553 (1996).

The donor moiety is excited by light of appropriate intensity within the excitation spectrum of the donor moiety ($\lambda_{excitation}$). The donor moiety emits the absorbed energy as fluorescent light ($\lambda_{emission\ 1}$). When the acceptor fluorescent protein moiety is positioned to quench the donor moiety in the excited state, the fluorescence energy is transferred to the acceptor moiety that can emit fluorescent light ($\lambda_{emission\ 2}$). FRET can be manifested as a reduction in the intensity of the fluorescent signal from the donor moiety ($\lambda_{emission\ 1}$), reduction in the lifetime of the excited state of the donor moiety, or emission of fluorescent light at the longer wavelengths (lower energies) characteristic of the acceptor moiety ($\lambda_{emission\ 2}$). When binding of the signal transduction protein to the transducisome protein occurs, the fluorescent protein moieties come closer, and FRET is increased.

The efficiency of FRET depends on the separation distance and the orientation of the donor and acceptor fluorescent protein moieties. For example, the Forster equation describes the efficiency of excited state energy transfer, based in part on the fluorescence quantum yield of the donor moiety and the energetic overlap with the acceptor moiety.

The Forster equation is:

$$E=(F_0-F)/F_0=R_0^6/(R^6+R_0^6)$$

where E is the efficiency of FRET, F and $F_0$ are the fluorescence intensities of the donor moiety in the presence and absence of the acceptor, respectively, and R is the distance between the donor moiety and the acceptor moiety.

The characteristic distance $R_0$ at which FRET is 50% efficient depends on the quantum yield of the donor moiety (i.e., the shorter-wavelength fluorophore), the extinction coefficient of the acceptor moiety (i.e., the longer-wavelength fluorophore), and the overlap between the emission spectrum of the donor moiety and the excitation spectrum of the acceptor moiety. $R_0$ is given (in Å) by:

$$R_0=9.79\times10^3(K^2QJn^{-4})^{1/6}$$

where $K^2$ is an orientation factor having an average value close to 0.67 for freely mobile donors and acceptors, Q is the quantum yield of the unquenched donor moiety, n is the refractive index of the medium separating the donor moiety and the acceptor moiety, and J is the overlap integral. J can be quantitatively expressed as the degree of spectral overlap between the donor moiety and the acceptor moiety according to the equation:

$$J=\int_0^\infty \mathring{a}_e F_e \ddot{e}^4 d\ddot{e}/\int_0^\infty F_e d\ddot{e}$$

where $\mathring{a}_e$, (M$^{-1}$ cm$^{-1}$) is the molar absorptivity of the acceptor and $F_{\lambda 2}$ is the donor moiety fluorescence intensity at wavelength ë. See, for example, Forster, T. *Ann.Physik* 2:55–75 (1948). Tables of spectral overlap integrals are readily available to those working in the field (for example, Berlman, I. B. *Energy transfer parameters of aromatic compounds*, Academic Press, New York and London (1973)). FRET is a nondestructive spectroscopic method that can monitor proximity and relative angular orientation of fluorophores in living cells. See, for example, Adams, S. R., et al., *Nature* 349:694–697 (1991), and Gonzalez, J. & Tsien, R. Y. *Biophy.J.* 69:1272–1280 (1995).

These factors need to be balanced to optimize the efficiency and detectability of FRET from assay systems described herein. The emission spectrum of the donor fluorescent protein moiety should overlap as much as possible with the excitation spectrum of the acceptor fluorescent protein moiety to maximize the overlap integral J. Also, the quantum yield of the donor fluorescent protein moiety and the extinction coefficient of the acceptor fluorescent protein moiety should be as large as possible to maximize $R_0$. In addition, the excitation spectra of the donor and acceptor moieties should overlap as little as possible so that a wavelength region can be found at which the donor moiety can be excited selectively and efficiently without directly exciting the acceptor moiety. Direct excitation of the acceptor moiety should be avoided since it can be difficult to distinguish direct emission from fluorescence arising from FRET. Similarly, the emission spectra of the donor and acceptor moieties should have minimal overlap so that the two emissions can be distinguished. High fluorescence quantum yield of the acceptor moiety is desirable if the emission from the acceptor moiety is to be monitored to determine the amount of its labeled protein in a sample. In a preferred embodiment, the donor fluorescent protein moiety is excited by ultraviolet (<400 nm) and emits blue light (<500 nm), and the acceptor fluorescent protein moiety is efficiently excited by blue but not by ultraviolet light and emits green light (>500 nm), for example, P4-3 and S65T, respectively.

In another preferred embodiment, the donor fluorescent moiety is excited by violet (400–430 nm) and emits blue-green (450–500 nm) and the acceptor fluorescent moiety is efficiently excited by blue-green (450–500 nm) and emits yellow-green light (?520 nm), for example WIB and 10C respectively.

The amount of a labeled protein in a sample can be determined by determining the degree of FRET in the sample. Labeled protein concentration can be determined by monitoring FRET at different concentrations to establish a calibration curve.

The degree of FRET can be determined by any spectral or fluorescence lifetime characteristic of the excited donor moiety. For example, intensity of the fluorescent signal from the donor, the intensity of fluorescent signal from the acceptor, the ratio of the fluorescence amplitudes near the acceptors emission maxima to the fluorescence amplitudes near the donor's emission maximum, or the excited state lifetime of the donor can be monitored.

Preferably, changes in the degree of FRET are determined as a function of the change in the ratio of the amount of fluorescence from the donor and acceptor moieties; a process referred to as "ratioing." Changes in the absolute amount of indicator, excitation intensity, and turbidity or other background absorbances in the sample at the excitation wavelength affect the intensities of fluorescence from both the donor and acceptor approximately in parallel. Therefore the ratio of the two emission intensities is a more robust and preferred measure of cleavage than either intensity alone.

Fluorescence in a sample is measured using a fluorometer. In general, excitation radiation, from an excitation source having a first wavelength, passes through excitation optics. The excitation optics cause the excitation radiation to excite the sample. In response, fluorescent proteins in the sample emit radiation which has a wavelength that is different from the excitation wavelength. Collection optics then collect the emission from the sample. The device can include a temperature controller to maintain the sample at a specific temperature while it is being scanned. According to one embodiment, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

Methods of performing assays on fluorescent materials are well known in the art and are described in, e.g., Lakowicz, J. R., *Principles of Fluorescence Spectroscopy*, New York: Plenum Press (1983); Herman, B., Resonance energy transfer microscopy, in: *Fluorescence Microscopy of Living Cells in Culture, Part B, Methods in Cell Biology*, vol. 30, ed. Taylor, D. L. & Wang, Y.-L., San Diego: Academic Press (1989), pp. 219–243; Turro, N. J., *Modern Molecular Photochemistry*, Menlo Park: Benjamin/Cummings Publishing Col, Inc. (1978), pp. 296–361.

The excited state lifetime of the donor moiety is, likewise, independent of the absolute amount of substrate, excitation intensity, or turbidity or other background absorbances. Its measurement requires equipment with nanosecond time resolution.

Quantum yields of wild-type GFP, S65T, and P4-1 mutants can be estimated by comparison with fluorescein in 0.1 N NaOH as a standard of quantum yield 0.91. J. N. Miller, ed., *Standards in Fluorescence Spectrometry*, New York: Chapman and Hall (1981). Mutants P4 and P4-3 were likewise compared to 9-aminoacridine in water (quantum yield 0.98).

Any fluorescent protein can be used in the invention, including proteins that fluoresce due intramolecular rearrangements or the addition of cofactors that promote fluorescence. For example, green fluorescent proteins of cnidarians, which act as their energy-transfer acceptors in bioluminescence, are suitable fluorescent proteins for use in the fluorescent indicators. A green fluorescent protein ("GFP") is a protein that emits green light, and a blue fluorescent protein ("BFP") is a protein that emits blue light. GFPs have been isolated from the Pacific Northwest jellyfish, *Aequorea victoria*, the sea pansy, *Renilla reniformis*, and *Phialidium gregarium*. See, Ward, W. W., et al., *Photochem. Photobiol.*, 35:803–808 (1982); and Levine, L. D., et al., *Comp. Biochem. Physiol.*, 72B:77–85 (1982).

A variety of *Aequorea*-related GFPs having useful excitation and emission spectra have been engineered by modifying the amino acid sequence of a naturally occurring GFP from *Aequorea victoria*. See, Prasher, D. C., et al., *Gene*, 111:229–233 (1992); Heim, R., et al., *Proc. Natl. Acad. Sci., USA*, 91:12501–04 (1994); U.S. Ser. No. 08/337,915, filed Nov. 10, 1994; International application PCT/US95/14692, filed Nov. 10, 1995; and U.S. Ser. No. 08/706,408, filed Aug. 30, 1996. The cDNA of GFP can be concatenated with those encoding many other proteins; the resulting fusions often are fluorescent and retain the biochemical features of the partner proteins. See, Cubitt, A. B., et al., *Trends Biochem. Sci.* 20:448–455 (1995). Mutagenesis studies have produced GFP mutants with shifted wavelengths of excitation or emission. See, Heim, R. & Tsien, R. Y. *Current Biol.* 6:178–182 (1996). Suitable pairs, for example a blue-shifted GFP mutant P4-3 (Y66H/Y145F) and an improved green mutant S65T can respectively serve as a donor and an acceptor for fluorescence resonance energy transfer (FRET). See, Tsien, R. Y., et al., *Trends Cell Biol.* 3:242–245 (1993). A fluorescent protein is an *Aequorea*-related fluorescent protein if any contiguous sequence of 150 amino acids of the fluorescent protein has at least 85% sequence identity with an amino acid sequence, either contiguous or non-contiguous, from the wild type *Aequorea* green fluorescent protein. More preferably, a fluorescent protein is an *Aequorea*-related fluorescent protein if any contiguous sequence of 200 amino acids of the fluorescent protein has at least 95% sequence identity with an amino acid sequence, either contiguous or non-contiguous, from the wild type *Aequorea* green fluorescent protein. Similarly, the fluorescent protein can be related to *Renilla* or *Phialidium* wild-type fluorescent proteins using the same standards.

Some *Aequorea*-related engineered versions described in Table I. Other variants or mutants are within the scope of the invention as described in the art or developed in the future.

TABLE I

| Clone | Mutation(s) | Excitation max (nm) | Emission max (nm) | Extinct. Coefficient ($M^{-1}$ $cm^{-1}$) | Quantum yield |
| --- | --- | --- | --- | --- | --- |
| Wild type | none | 395 (475) | 508 | 21,000 (7,150) | 0.77 |
| P4 | Y66H | 383 | 447 | 13,500 | 0.21 |
| P4-3 | Y66H; Y145F | 381 | 445 | 14,000 | 0.38 |
| W7 | Y66W; N146I M153T V163A N212K | 433 (453) | 475 (501) | 18,000 (17,100) | 0.67 |
| W2 | Y66W; I123V Y145H H148R | 432 (453) | 480 | 10,000 (9,600) | 0.72 |

TABLE I-continued

| Clone | Mutation(s) | Excitation max (nm) | Emission max (nm) | Extinct. Coefficient ($M^{-1}$ $cm^{-1}$) | Quantum yield |
|---|---|---|---|---|---|
| | M153T<br>V163A<br>N212K | | | | |
| S65T | S65T | 489 | 511 | 39,200 | 0.68 |
| P4-1 | S65T; M153A<br>K238E | 504 (396) | 514 | 14,500 (8,600) | 0.53 |
| S65A | S65A | 471 | 504 | | |
| S65C | S65C | 479 | 507 | | |
| S65L | S65L | 484 | 510 | | |
| Y66F | Y66F | 360 | 442 | | |
| Y66W | Y66W | 458 | 480 | | |
| 10c | S65G; V68L<br>S72A; T203Y | 513 | 527 | | |
| WIB | F64L; S65T<br>Y66W; N146I<br>M153T<br>V163A<br>N212K | 432 (453) | 476 (503) | | |
| Emerald | S65T; S72A<br>N149K<br>M153T<br>I167T | 487 | 508 | | |
| Sapphire | S72A; Y145F<br>T203I | 395 | 511 | | |

Other fluorescent proteins can be used in the proteins of the invention, such as, for example, yellow fluorescent protein from *Vibrio fischeri* strain Y-1, Peridinin-chlorophyll a binding protein from the dinoflagellate *Symbiodinium* sp.phycobiliproteins from marine cyanobacteria such as *Synechococcus*, e.g., phycoerythrin and phycocyanin, or oat phytochromes from oat reconstructed with phycoerythrobilin. These fluorescent proteins have been described in Baldwin, T. O., et al., *Biochemistry* 29:5509–5515 (1990), Morris, B. J., et al., *Plant Molecular Biology*, 24:673–677 (1994), and Wilbanks, S. M., et al., *J. Biol. Chem.* 268:1226–1235. (1993), and Li et al., *Biochemistry* 34:7923–7930 (1995).

A localization sequence may be used to enhance targeting the transducisome or signal transduction protein to a predetermined cellular location. Localization sequences can be targeting sequences which are described, for example, in "Protein Targeting", chapter 35 of Stryer, L., *Biochemistry* (4th ed.). W. H. Freeman, 1995. The localization sequence can also be a localized protein. Some important localization sequences include those targeting the nucleus KKKRK (SEQ ID NO:13), mitochondrion (amino terminal MLRTSS-LFTRRVQPSLFRNILRLQST (SEQ ID NO:14), endoplasmic reticulum (KDEL (SEQ ID NO:15) at C-terminus, assuming a signal sequence present at N-terminus), peroxisome (SKF at C-terminus), prenylation or insertion into plasma membrane (CaaX, CC, CXC, or CCXX (SEQ ID NO:16), at C-terminus), cytoplasmic side of plasma membrane (fusion to SNAP-25), or the Golgi apparatus (fusion to furin).

Production of Assay Systems and Proteins of the Invention Using Cells

Many of the assays systems and proteins described herein can be produced as fusion proteins, heterologously expressed proteins and endogenous expressed proteins by recombinant DNA technology, molecular biology and cell biology or a combination thereof. Recombinant and cellular production of fluorescent proteins, transducisomes and signal transduction involves expressing nucleic acids having sequences that encode the proteins. Nucleic acids encoding transducisome proteins can be obtained by methods known in the art. For example, a nucleic acid encoding other transducisome proteins can be isolated by polymerase chain reaction of cDNA from various tissues and organism using primers based on the DNA sequences of proteins containing PDZ domains or using cDNA probes from the same. PCR methods are described in, for example, U.S. Pat. No. 4,683, 195; Mullis, et al. *Cold Spring Harbor Symp. Quant. Biol.* 51:263 (1987), and Erlich, ed., *PCR Technology*, (Stockton Press, NY, 1989). In addition to such cloning approaches to find new or orphan transducisomes, amino acid sequences in existing databases such as GENBANK or EMBL, can be scanned for proteins having PDZ domains and the protein sequences analyzed as described herein. Putative or orphan transducisomes can be readily screened with known signal transduction proteins to find their corresponding transducisome protein. Many of the assays described herein are particularly suitable for such screening.

Mutant versions of transducisomes can be made by site-specific mutagenesis of nucleic acids encoding transducisome proteins (particularly PDZ domains), or by random mutagenesis caused by increasing the error rate of PCR of the original polynucleotide with 0.1 mM $MnCl_2$ and unbalanced nucleotide concentrations. Other mutant screening methods as known in the art, developed in the future or described herein can be used. Such mutants can be readily tested for their ability to decrease binding to signal transduction proteins. Such defective transducisome proteins can be used as controls in the assays described herein, both as controls in biochemical assays and in cell-based assays (e.g., cell lines with defective transducisomes as described herein). New fluorescent proteins can also be made by mutagenesis.

The construction of expression vectors and the expression of genes in transfected cells involve the use of molecular cloning techniques also well known in the art. Sambrook et al., *Molecular Cloning—A Laboratory Manual*, Cold Spring Harbor Laboratory, Cold Spring Harbor, N.Y., (1989) and *Current Protocols in Molecular Biology*, F. M. Ausubel et al., eds., (Current Protocols, a joint venture between Greene Publishing Associates, Inc. and John Wiley & Sons, Inc., most recent Supplement).

Nucleic acids used to transfect cells with sequences coding for expression of the polypeptide of interest generally will be in the form of an expression vector including expression control sequences operatively linked to a nucleotide sequence coding for expression of the polypeptide. As used, the term "nucleotide sequence coding for expression of" a polypeptide refers to a sequence that, upon transcription and translation of mRNA, produces the polypeptide. This can include sequences containing, e.g., introns. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

Methods which are well known to those skilled in the art can be used to construct expression vectors comprising a transducisome protein or signal transduction protein coding sequence, or both, and appropriate transcriptional/translational control signals. These methods include in vitro recombinant DNA techniques, synthetic techniques and in vivo recombination/genetic recombination. (See, for example, the techniques described in Maniatis, et al., *Molecular Cloning A Laboratory Manual*, Cold Spring Harbor Laboratory, N.Y., 1989).

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransfected with DNA sequences encoding the fusion polypeptide of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Gluzman ed., 1982). Preferably, a cukaryotic host is utilized as the host cell as described herein.

Techniques for the isolation and purification of either microbially or eukaryotically expressed polypeptides of the invention may be by any conventional means such as, for example, preparative chromatographic separations and immunological separations such as those involving the use of monoclonal or polyclonal antibodies or antigen.

A variety of host-expression vector systems may be utilized to express transducisome protein or signal transduction protein coding sequence or both. These include but are not limited to microorganisms such as bacteria transformed with recombinant bacteriophage DNA, plasmid DNA or cosmid DNA expression vectors containing a protein of the invention coding sequence; yeast transformed with recombinant yeast expression vectors containing the a protein of the invention coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a protein of the invention coding sequence; insect cell systems infected with recombinant virus expression vectors (e.g., baculovirus) containing a transducisome protein or signal transduction protein coding sequence, or both; or animal cell systems infected with recombinant virus expression vectors (e.g., retroviruses, adenovirus, vaccinia virus) containing a transducisome protein or signal transduction protein coding sequence, or both, or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (see, e.g., Bitter, et al., Methods in Enzymology 153:516–544, 1987). For example, when cloning in bacterial systems, inducible promoters such as pL of bacteriophage ?, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted transducisome protein or signal transduction protein coding sequence, or both.

In bacterial systems a number of expression vectors may be advantageously selected depending upon the use intended for the transducisome protein or signal transduction protein coding sequence expressed. For example, when large quantities of the transducisome protein or signal transduction protein are to be produced, vectors which direct the expression of high levels of fusion protein products that are readily purified may be desirable. Those which are engineered to contain a cleavage site to aid in recovering transducisome protein or signal transduction protein coding sequence are preferred.

In yeast, a number of vectors containing constitutive or inducible promoters may be used. For a review see, Current Protocols in Molecular Biology, Vol. 2, Ed. Ausubel, et al., Greene Publish. Assoc. & Wiley Interscience, Ch. 13, 1988; Grant, et al., Expression and Secretion Vectors for Yeast, in Methods in Enzymology, Eds. Wu & Grossman, 31987, Acad. Press, N.Y., Vol. 153, pp.516–544, 1987; Glover, DNA Cloning, Vol. II, IRL Press, Wash., D.C., Ch. 3, 1986; and Bitter, Heterologous Gene Expression in Yeast, Methods in Enzymology, Eds. Berger & Kimmel, Acad. Press, N.Y., Vol. 152, pp. 673–684, 1987; and The Molecular Biology of the Yeast *Saccharomyces*, Eds. Strathern et al., Cold Spring Harbor Press, Vols. I and II, 1982. A constitutive yeast promoter such as ADH or LEU2 or an inducible promoter such as GAL may be used (Cloning in Yeast, Ch. 3, R. Rothstin In: DNA Cloning Vol.11, A Practical Approach, Ed. D M Glover, IRL Press, Wash., D.C., 1986). Alternatively, vectors may be used which promote integration of foreign DNA sequences into the yeast chromosome.

In cases where plant expression vectors are used, the expression of a transducisome protein or signal transduction protein coding sequence may be driven by any of a number of promoters. For example, viral promoters such as the 35S RNA and 19S RNA promoters of CaMV (Brisson, et al., *Nature* 310:511–514, 1984), or the coat protein promoter to TMV (Takamatsu, et al., *EMBO J.* 6:307–311, 1987) may be used; alternatively, plant promoters such as the small subunit of RUBISCO (Coruzzi, et al., 1984, *EMBO J.* 3:1671–1680; Broglie, et al., *Science* 224:838–843, 1984); or heat shock promoters, e.g., soybean hsp17.5-E or hsp17.3-B (Gurley, et al., Mol. Cell. Biol. 6:559–565, 1986) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, *Methods for Plant Molecular Biology*, Academic Press, NY, Section VIII, pp. 421–463, 1988; and Grierson & Corey, *Plant Molecular Biology*, 2d Ed., Blackie, London, Ch. 7–9, 1988.

An alternative expression system which could be used to express a transducisome protein or signal transduction protein coding sequence is an insect system. In one such system, *Autographa californica* nuclear polyhedrosis virus (AcNPV) is used as a vector to express foreign genes. The virus grows in *Spodoptera frugiperda* cells. The transducisome protein or signal transduction protein coding sequences may be cloned into non-essential regions (for example, the polyhedrin gene) of the virus and placed under control of an AcNPV promoter (for example the polyhedrin promoter). Successful insertion of the transducisome protein or signal transduction protein coding sequence coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed, see Smith, et al., *J. Viol.* 46:584, 1983; Smith, U.S. Pat. No. 4,215,051.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and, advantageously secretion of the gene product should be used as host cells for the expression of proteins of the invention. Such host cell lines may include but are not limited to CHO, VERO, BHK, HeLa, COS, MDCK, Jurkat, HEK-293, and WI38.

Mammalian cell systems which utilize recombinant viruses or viral elements to direct expression may be engineered. For example, when using adenovirus expression vectors, the transducisome protein or signal transduction protein coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the proteins of the invention in infected hosts (e.g., see Logan & Shenk, *Proc. Natl. Acad. Sci. USA*, 81: 3655–3659, 1984). Alternatively, the vaccinia virus 7.5K promoter may be used. (e.g., see, Mackett, et al., *Proc. Natl. Acad. Sci. USA*, 79: 7415–7419, 1982; Mackett, et al., J. Virol. 49: 857–864, 1984; Panicali, et al., *Proc. Natl. Acad. Sci. USA* 79: 4927–4931, 1982). Of particular interest are vectors based on bovine papilloma virus which have the ability to replicate as extrachromosomal elements (Sarver, et al., *Mol. Cell. Biol.* 1: 486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the fluorescent indicator gene in host cells (Cone & Mulligan, *Proc. Natl. Acad. Sci. USA*, 81:6349–6353, 1984). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the transducisome protein or signal transduction protein cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler, et al., *Cell*, 11: 223, 1977), hypoxanthine-guanine phosphoribosyltransferase (Szybalska & Sybalski, *Proc. Natl. Acad. Sci. USA*, 48:2026, 1962), and adenine phosphoribosyltransferase (Lowy, et al., *Cell*, 22: 817, 1980) genes can be employed in tk⁻, hgprt or aprt cells respectively. Also, antimetabolite resistance can be used as the basis of selection for dhfr, which confers resistance to methotrexate (Wigler, et al., Proc. Natl. Acad. Sci. USA, 77: 3567, 1980; O'Hare, et al., *Proc. Natl. Acad. Sci. USA*, 8: 1527, 981); gpt, which confers resistance to mycophenolic acid (Mulligan & Berg, *Proc. Natl. Acad. Sci. USA*, 78: 2072, 1981; neo, which confers resistance to the aminoglycoside G-418 (Colberre-Garapin, et al., *J. Mol. Biol.*, 150:1, 1981); and hygro, which confers resistance to hygromycin (Santerre, et al., *Gene*, 30: 147, 1984) genes. Recently, additional selectable genes have been described, namely trpB, which allows cells to utilize indole in place of tryptophan; hisD, which allows cells to utilize histinol in place of histidine (Hartman & Mulligan, *Proc. Natl. Acad. Sci. USA*, 85:8047, 1988); and ODC (ornithine decarboxylase) which confers resistance to the ornithine decarboxylase inhibitor, 2-(difluoromethyl)-DL-ornithine, DFMO (McConlogue L., In: *Current Communications in Molecular Biology*, Cold Spring Harbor Laboratory, ed., 1987).

DNA sequences encoding the transducisome protein or signal transduction protein coding sequence polypeptide of the invention can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, in other words when the foreign DNA is continuously maintained in the host, are known in the art.

Recombinant transducisome protein or signal transduction protein coding sequence can be produced by expression of nucleic acid encoding the protein in prokaryotes, such as E. coli or in eukaryotes, such as yeast cells or mammalian cells.

The construct can also contain a tag to simplify isolation of the transducisome protein or signal transduction protein coding sequence. For example, a polyhistidine tag of, e.g., six histidine residues, can be incorporated at the amino terminal end of the fluorescent protein. The polyhistidine tag allows convenient isolation of the protein in a single step by nickel-chelate chromatography.

In a preferred embodiment, the transducisome protein or signal transduction protein coding sequence is a fusion protein with a fluorescent protein produced by recombinant DNA technology in which a single polypeptide includes a donor moiety, a peptide linker moiety or an acceptor moiety and a peptide linker moiety. The donor moiety can be positioned at the amino-terminus relative to the acceptor moiety in the polypeptide. Such a fusion protein has the generalized structure: (amino terminus) donor or acceptor fluorescent protein moiety—peptide linker moiety—transducisome protein or signal transduction protein (carboxy terminus). Alternatively, the donor moiety can be positioned at the carboxy-terminus of the transducisome protein or signal transduction protein. To optimize the location of the donor and acceptor for a particular binding pair of transiducisome protein and signal transduction protein all combinations (such as N-donor-C-N-transducisome protein-C-N-acceptor-C-N-signal transduction protein-C, N-transducisome protein-C-N-donor-C/N-acceptor-C-N-signal transduction protein-C, N-donor-C-N-transducisome protein-C/N-signal transduction protein-C-N-acceptor-C, N-transducisome protein-C-N-donor-C/N-signal transduction protein-C-N-acceptor-C, N-acceptor-C-N-transducisome-C/N-donor-C-N-signal transduction protein-C, and N-transducisome-C-N-acceptor-C/N-donor-C-N-signal transduction protein-C) can be readily made and tested within a short period of time or person days. Tranducisome protein fragments and signal transduction fragments can be made this way as well. The invention also envisions fusion proteins that contain extra amino acid sequences at the amino and/or carboxy termini, for example, polyhistidine tags. Such fluorescent transducisome and signal transduction proteins or fragments thereof can also be used as non-FRET proteins in fluorescent binding assays for screening compounds.

Thus, FRET binding pair of transducisome protein and signal transduction proteins can be encoded by a recombinant nucleic acid sequences. The elements are selected so that upon expression into fusion proteins, the donor and acceptor moieties exhibit FRET when the donor moiety is excited and binding occurs. The recombinant nucleic acid can be incorporated into an expression vector comprising expression control sequences operatively linked to the recombinant nucleic acid. The expression vector can be adapted for function in prokaryotes or eukaryotes by inclusion of appropriate promoters, replication sequences, markers, etc.

The expression vector can be transfected into a host cell for expression of the recombinant nucleic acid. Host cells can be selected for high levels of expression in order to purify the fluorescent binding pair of transducisome protein and signal transduction proteins. E. coli is useful for this purpose, especially if larger quantities of full-length proteins or functionally fragments are desired for biochemical assays. Alternatively, the host cell can be a prokaryotic or eukaryotic cell selected to study the activity of an enzyme produced by the cell. In this case, the linker peptide is selected to include an amino acid sequence recognized by the protease. The cell can be, e.g., a cultured cell or a cell in vivo.

A primary advantage of proteins of the invention is that they are prepared by normal protein biosynthesis, thus completely avoiding organic synthesis and the requirement for customized unnatural amino acid analogs. The constructs can be expressed in E. coli in large scale for in vitro assays. Purification from bacteria is simplified when the sequences include polyhistidine tags for one-step purification by nickel-chelate chromatography. Alternatively, the substrates can be expressed directly in a desired host cell for assays in situ, as described herein for screening assays.

Cells and Targets

Any cell expressing a protein target in sufficient quantity for measurement in cellular assays can be used with the invention. Cells endogenously expressing proteins of the invention are suitable for many embodiments, as well as proteins expressed from heterologous nucleic acids. For example, cells may be transfected with a suitable vector encoding one or more targets that are known to those of skill in the art or may be identified by those of skill in the art. Although essentially any cell which expresses endogenous ion channel or receptor activity may be used, when using receptors or channels as targets it is preferred to use cells transformed or transfected with heterologous DNAs encoding such ion channels and/or receptors so as to express predominantly a single type of ion channel or receptor. Many cells that may be genetically engineered to express a heterologous cell surface protein are known. Exemplary membrane proteins include, but are not limited to, surface receptors and ion channels.

One method of the present invention uses targets for identifying chemicals that are useful in modulating the activity of a target in the presence of a transducisome protein. The target can be any biological entity, such as a protein, sugar, nucleic acid or lipid. Typically, targets will be proteins such as cell surface proteins or enzymes. Targets can be assayed in either biochemical assays (targets free of cells), or cell based assays (targets associated with a cell).

For example, cells expressing transducisome proteins may be loaded with ion or voltage sensitive dyes to report receptor or ion channel activity, such as calcium channels or N-methyl-D-aspartate (NMDA) receptors, GABA receptors, kainate/AMPA receptors, nicotinic acetylcholine receptors, sodium channels, calcium channels, potassium channels excitatory amino acid (EAA) receptors, and nicotinic acetylcholine receptors. Assays for determining activity of such receptors can also use agonists and antagonists to use as negative or positive controls to assess activity of tested chemicals. In preferred embodiments of automated assays for identifying chemicals that have the capacity to modulate the function of receptors or ion channels (e.g., agonists, antagonists), changes in the level of ions in the cytoplasm or membrane voltage will be monitored using an ion-sensitive or membrane voltage fluorescent indicator, respectively. Among the ion-sensitive indicators and voltage probes that may be employed, are those disclosed in the Molecular Probes 1997 Catalog, herein incorporated by reference.

Other methods of the present invention concern determining the activity of receptors in the presence of transducisome proteins. Receptor activation can sometimes initiate subsequent intracellular events that release intracellular stores of calcium ions for use as a second messenger. Activation of some G-protein-coupled receptors stimulates the formation of inositol triphosphate (IP3 a G-protein coupled receptor second messenger) through phospholipase C-mediated hydrolysis of phosphatidylinositol, Berridge and Irvine (1984), Nature 312: 315–21. IP3 in turn stimulates the release of intracellular calcium ion stores. Thus, a change in cytoplasmic calcium ion levels caused by release of calcium ions from intracellular stores can be used to reliably determine G-protein-coupled receptor function. Among G-protein-coupled receptors are muscarinic acetylcholine receptors (mAChR), adrenergic receptors, serotonin receptors, dopamine receptors, angiotensin receptors, adenosine receptors, bradykinin receptors, metabotropic excitatory amino acid receptors and the like. Cells expressing such G-protein-coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores.

Other assays can involve determining the activity of receptors in the presence of transducisome proteins which, when activated, result in a change in the level of intracellular cyclic nucleotides, e.g., cAMP, cGMP. For example, activation of some dopamine, serotonin, metabotropic glutamate receptors and muscarinic acetylcholine receptors results in a decrease in the cAMP or cGMP levels of the cytoplasm. Furthermore, there are cyclic nucleotide-gated ion channels, e.g., rod photoreceptor cell channels and olfactory neuron channels (see, Altenhofen, W. et al. (1991) Proc. Natl. Acad. Sci U.S.A. 88:9868–9872 and Dhallan et al. (1990) Nature 347: 184–187) that are permeable to cations upon activation by binding of cAMP or cGMP. In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cells for this type of assay can be made by co-transfection of a host cell with DNA encoding a cyclic nucleotide-gated ion channel, transducisome protein and DNA encoding a receptor (e.g., certain metabotropic glutamate receptors, muscarinic acetylcholine receptors, dopamine receptors, serotonin receptors, and the like), which, when activated, causes a change in cyclic nucleotide levels in the cytoplasm.

Ion channels can also be used with the invention and include, but are not limited to, calcium channels comprised of the human calcium channel $\alpha_2\beta$ and/or $\gamma$-subunits (see also, WO89/09834; human neuronal $\alpha_2$ subunit); rabbit skeletal muscle al subunit (Tanabe, et al. (1987) Nature 328, pp. 313–E318); rabbit skeletal muscle $\alpha_2$ subunit (Ellis, et al. (1988) Science 241, pp. 1661–1664); rabbit skeletal muscle p subunit (Ruth, et al. (1989) Science 245, pp. 1115–1118); rabbit skeletal muscle $\gamma$ subunit (Jay, et al. (1990) Science 248, pp. 490–492); and the like; potassium ion channels, e.g., rat brain (BK2) (McKinnon, D. (1989) J. Biol Chem. 264, pp. 9230–8236); mouse brain (BK1) (Tempel, et al. (1988) Nature 332, pp. 837–839); and the like; sodium ion channels, e.g., rat brain I and II (Noda, et al. (1986) Nature 320, pp. 188–192); rat brain III (Kayano, et al. (1988) FEBS Lett. 228, pp. 187–1.94); human II (ATCC No. 59742, 59743 and Genomics 5: 204–208 (1989); chloride ion channels (Thiemann, et al. (1992), Nature 356, pp. 57–60 and Paulmichl, et al. (1992) Nature 356, pp. 238–241), and others known or developed in the art.

GPCRs that can be used with the invention include, but are not limited to, muscarinic receptors, e.g., human M2 (GenBank accession #M16404); rat M3 (GenBank accession #M16407); human M4 (GenBank accession #M16405); human M5 (Bonner, et al., (1988) Neuron 1, pp. 403–410); and the like; neuronal nicotinic acetylcholine receptors, e.g., the human $\alpha_2$, $\alpha_3$, and $\beta_2$, subtypes. The human $\alpha_5$ subtype (Chini, et al. (1992) Proc. Natl. Acad. Sci. U.S.A. 89: 1572–1576), the rat $\alpha_2$ subunit (Wada, et al. (1988) Science 240, pp. 330–334); the rat $\alpha_3$ subunit (Boulter, et al. (1986) Nature 319, pp. 368–374); the rat $\alpha_4$ subunit (Goldman, et al. (1987) Cell 48, pp. 965–973); the rat $\alpha_5$ subunit (Boulter, et al. (1990) I. Biol. Chem. 265, pp. 4472–4482); the chicken $\alpha_7$ subunit (Couturier et al. (1990) Neuron 5: 847–856); the rat $\beta_2$ subunit (Deneris, et al. (1988) Neuron 1, pp. 45–54) the rat $\beta_3$ subunit (Deneris, et al. (1989) J. Biol. Chem. 264, pp. 6268–6272); the rat $\beta_4$ subunit (Duvoisin, et al. (1989) Neuron 3, pp. 487–496); combinations of the rat $\alpha$ subunits, and s$\beta$ subunits and a and p subunits; GABA receptors, e.g., the bovine x, and $\beta_1$, subunits (Schofield, et al. (1987) Nature 328, pp. 221–227); the bovine $X_2$, and $X_3$, subunits (Levitan, et al. (1988) Nature 335, pp. 76–79); the $\gamma$-subunit (Pritchett, et al. (1989) Nature 338, pp. 582–585); the $\beta_2$, and $\beta_3$, subunits (Ymer, et al. (1989) EMBO J. 8, pp. 1665–1670); the 8 subunit (Shivers, B. D. (1989) Neuron 3, pp. 327–337); and the like; glutamate receptors, e.g., rat GluR1 receptor (Hollman, et al. (1989) Nature 342, pp. 643–648); rat GluR2 and GluR3 receptors (Boulter et al. (1990) Science 249:1033–1037; rat GluR4 receptor (Keinanen et al. (1990) Science 249: 556–560); rat GluR5 receptor (Bettler et al. (1990) Neuron 5: 583–595); rat GluR6 receptor (Egebjerg et al. (1991) Nature 351: 745–748); rat GluR7 receptor (Bettler et al. (1992) neuron 8:257–265); rat NMDAR1 receptor (Moriyoshi et al. (1991) Nature 354:31–37 and Sugihara et al. (1992) Biochem. Biophys. Res. Comm. 185:826–832); mouse NMDA el receptor (Meguro et al. (1992) Nature 357: 70–74); rat NMDAR2A, NMDAR2B and NMDAR2C receptors (Monyer et al. (1992) Science 256: 1217–1221); rat metabotropic mGluR1 receptor (Houamed et al. (1991) Science 252: 1318–1321); rat metabotropic mGluR2, mGluR3 and mGluR4 receptors (Tanabe et al. (1992) Neuron 8:169–179); rat metabotropic mGluR5 receptor (Abe et al. (1992) I. Biol. Chem. 267: 13361–13368); and the like; adrenergic receptors, e.g., human $\beta1$ (Frielle, et al. (1987) Proc. Natl. Acad. Sci. 84, pp. 7920–7924); human $\alpha_2$ (Kobilka, et al. (1987) Science 238, pp. 650–656); hamster$_2\beta$ (Dixon, et al. (1986) Nature 321, pp. 75–79); and the like; dopamine receptors, e.g., human D2 (Stormann, et al. (1990) Molec. Pharm. 37, pp. 1–6); mammalian dopamine D2 receptor (U.S. Pat. No. 5,128,254); rat (Bunzow, et al. (1988) Nature 336, pp. 783–787); and the like; and the like; serotonin receptors, e.g., human 5HT1a (Kobilka, et al. (1987) Nature 329, pp. 75–79); serotonin 5HT1C receptor (U.S. Pat. No. 4,985,352); human 5HT1D (U.S. Pat. No. 5,155,218); rat 5HT2 (Julius, et al. (1990) PNAS 87, pp.928–932); rat 5HT1c (Julius, et al. (1988) Science 241, pp. 558–564), and the like.

Various methods of identifying activity of chemical with respect to a target in the presence of a transducisome protein can be applied, including: ion channels (PCT publication WO 93/13423), cell surface receptors (U.S. Pat. Nos. 5,401, 629, and 5,436,128 and PCT Application WO 93/13423 (Akong et al) and intracellular receptors (PCT publication WO 96/41013, U.S. Pat. Nos. 5,548,063, 5,171,671, 5,274, 077, 4,981,784, EP 0 540 065 A1, U.S. Pat. Nos. 5,071,773, and 5,298,429). All of the foregoing references are herein incorporated by reference in their entirety.

If desired (e.g., for commercial purposes), a cell(s) of the invention can packaged into a container that is packaged within a kit. Such a kit may also contain any of the various isolated nucleic acids, antibodies, proteins, signal transduction detection systems, substrates, and/or drugs described herein, known in the art or developed in the future. A typical kit also includes a set of instructions for any or all of the methods described herein.

EXAMPLES

The following examples are intended to illustrate but not limit the invention. While examples are typical of those methods compositions that might be used to practice the invention, other procedures known to those skilled in the are may alternatively be used as appropriate.

Example 1

Materials and Methods Used in the Examples
Mutant Screens and Western Blots

Males of cn bw genotype were aged for 5 days, treated with EMS, and crossed en masse to flies carrying the dominant temperature sensitive DTS91 allele. Single F1 males were collected and crossed in single vials to CyO/DTS91 virgin females. The vials were then shifted to 29° C. for 72 hrs to eliminate any eggs or larvae carrying the DTS allele. The parents were then removed and the vials were incubated at 29° C. for an additional 48 hrs before returning to 25° C. The progeny from this cross were transferred to fresh food, and their homozygous white-eyed offspring (cn bw) were subjected to a protein immunoblot screen for the loss of the INAD antigen[33].
Antibodies To generate antibodies specific to INAD, we generated a T7-fusion protein consisting of the last 300 residues of the protein. All antibodies were checked for specificity and affinity using wild type, mutant, and transgenic controls. For immunostaining, the INAD antibody was diluted 1:500 in phosphate buffered saline, 1% BSA, 0.1% saponin (PBS-S); the TRP antibody was first preabsorbed with a homogenate of trp mutant heads to reduce background staining and used at a final dilution of 1:100. Rhodopsin (1:300), eye-PKC (1:50), PLC (1:1000), TRPL (1:100), and DGq (1:200) were detected using polyclonal antibodies as previously described[33,34,44].
Immunoprecipitation Frozen heads (500–1,000) were homogenized in 2 to 3 mL of buffer A (50 mM Tris-HCl (pH 7.5), 50 mM NaCl, 1 mM EDTA and protease inhibitors) using a glass-glass homogenizer. The homogenate was centrifuged at 4,000×g for one minute to remove chitinous material. Membranes were isolated by centrifugation at 100,000×g for 30 minutes at 4° C., and resuspended in 0.8 to 1 ml of buffer A to determine protein concentration. Samples were re-centrifuged, resuspended in buffer B (150 mM NaCl, 1% triton, 50 mM Tris-HCl, pH 8.0 and protease inhibitors), mixed (100 μg of protein) with anti-INAD antibodies and incubated for 1 hour at 4° C. At this time, 30 μl of protein A-agarose beads (Pierce) were added and incubated for 2 additional hours. Samples were washed in buffer B, resuspended in SDS buffer and fractionated by SDS PAGE. The entire immunoprecipitate was loaded on the gels. Studies using GST-INAD protein fusions used similar incubation conditions but also contained affinity-purified GST-fusion proteins. GST-fusions containing individual PDZ domains (PDZ1 to PDZ5) were constructed according to the boundaries shown in FIG. 2. All GST-fusions were overproduced and purified by affinity chromatography on glutathione-agarose beads as described[19,23,50].

Electrophysiological Recordings

Photoreceptors were isolated from adult flies (<6 hr after eclosion) and whole-cell, patch-clamp recordings were performed as previously described[33]. Photoreceptors were stimulated by a 75 W Xenon source connected to the epifluorescence port of an inverted Fluovert FS (Leitz) microscope; light was bandpass-filtered ($\lambda$?=580±10 nm) and focused onto the photoreceptor cells with a 0.5 numerical aperture, 40× objective. Signals were recorded with an Axopatch 200A patch-clamp amplifier (Axon Instruments, Foster City, Calif.) and data were analyzed using pClamp6.02 (Axon) and Origin (Microcal) software. The membrane of the photoreceptors was voltage-clamped at a holding potential of −40 mV. Traces were low-pass filtered at 2 kHz (Bessel filter) and digitized at 2 kHz, unless stated otherwise. Measured series resistance, 16 MΩ on average, was 80% compensated. The bath solution contained (in mM): 124 NaCl, 4 KCL, 10 HEPES, 5 proline, 25 sucrose, 1.5 $CaCl_2$, 1 $MgCl_2$, pH 7.15. Pipette solution contained 95 K Gluconate, 40 KCl, 10 mM HEPES, 2 $MgCl_2$, 2 EGTA, pH 7.15.

For quantum-bump analysis, photoreceptors were clamped at −70 mV, and stimulated with a dim light flash to generate quantum bumps around 50% of the time. Signals were lowpass-filtered at 1 kHz and digitized at 2 kHz.

Example 2

Exemplary Transducisome Structure

To investigate a putative transducisome and its structure, the inventors analyzed the protein structure of INAD (SEQ. ID NO.: 1). INAD was selected as a candidate transducisome because mutants in the gene, InaD, produce a dominant negative phenotype for photoreceptor activation. The primary structure of INAD was analyzed using BLAST. INAD is a modular protein composed of five closely linked PDZ domains (see FIG. 2). Each of these domains contains the structural hallmarks of a prototypical PDZ motif, including the conserved amino acid region target binding. Each PDZ domains, however, is different and displays sufficient differences in amino acid sequence to permit binding of different signal transduction proteins and to allow distinct protein-protein interactions. This finding was quite surprising, as previous studies had shown that INAD contains two PDZ domains instead of five.

Figures 2A, 2B:
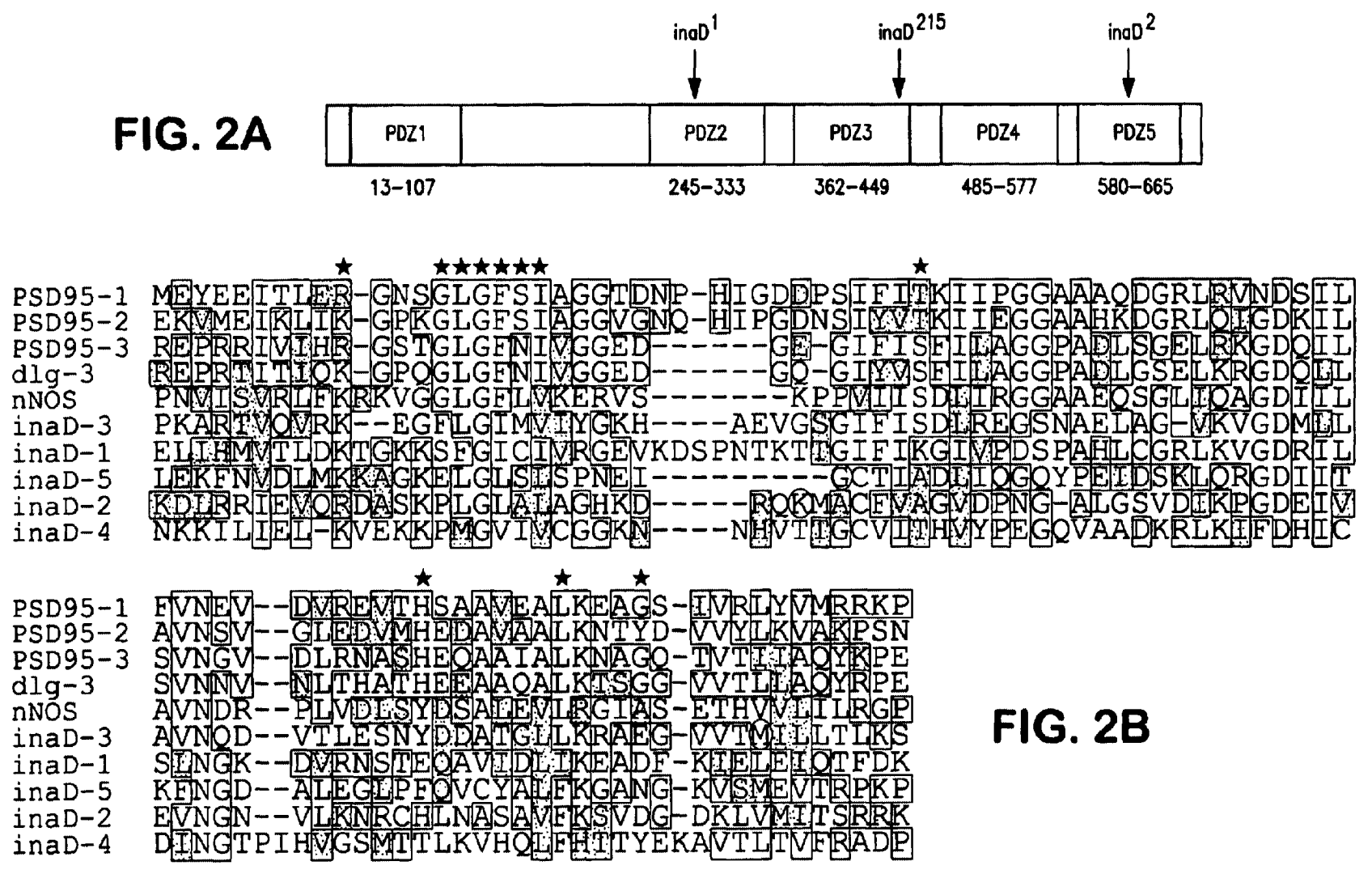

FIG. 2A shows a diagram of INAD protein with the locations of and size of each PDZ domain highlighted. Also shown is the relative location of the three InaD mutations related to photoreceptor activation.

FIG. 2B shows an amino acid alignment of PDZ domains from mammalian PSD-95[9], nNOS[23], Drosophila dlg[8] and inaD[36]. Sequences were aligned to maximize similarities and the full-length sequences of the references are herein incorporated by reference. Black boxes indicate amino acid identities and gray boxes show conservative substitutions. Stars above the sequence indicate residues implicated in substrate binding[27]. The circled residues refer to the site of point mutation in the three Drosophila inaD alleles.

Figure 2C:
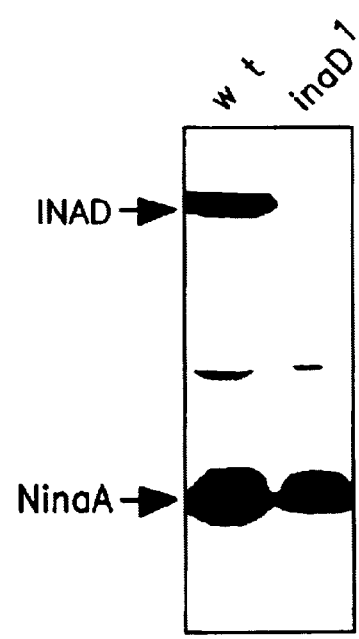
FIG. 2C shows an immunoblot demonstrating the absence of INAD protein in inaD[1].

FIG. 2C shows an immunoblot demonstrating the absence of INAD protein in inaD[1]. Another photoreceptor protein NinaA was used as a control in the blots. Note normal levels of NinaA in both lanes.

Example 3

Transducisomes Organize Signal Transduction in a Membranes

To investigate the ability of transducisomes to organize signal transduction proteins in membranes, the inventors measured binding of signal transduction proteins to INAD. The inventors assayed for binding of different phototransduction cascade proteins to INAD. Immunoprecipitations and GST-INAD protein fusions were used to identify INAD binding entities or targets.

Figure 3A:
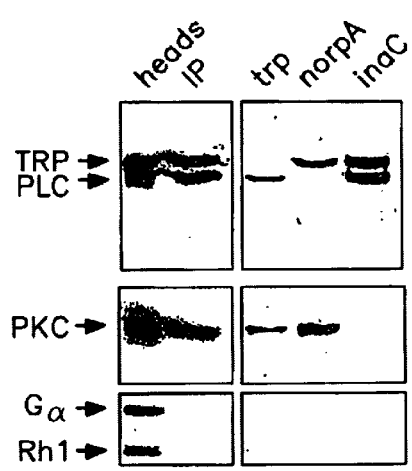
FIG. 3A shows that INAD antibodies co-immunoprecipitate TRP, eye-PKC and $PLC_\beta$ from retinal extracts in an immunoblot.

FIG. 3A shows that INAD antibodies co-immunoprecipitate TRP, eye-PKC and PLC$_\beta$ from retinal extracts[38]. Rhodopsin and Gq$_a$ failed to immunoprecipate despite the fact that both proteins are extremely abundant in photoreceptor cells. Membranes prepared from the heads of wt flies (IP) or trp, norpA and inaC mutants were immunoprecipitated (100 ug) with anti-INAD antibody as described in Example 1. The immunoprecipitated proteins were separated by SDS-PAGE, transferred to nitrocellulose and separately probed with antibodies specific for TRP, PLC, eye-PKC, G alpha subunit (G$\alpha$) and rhodopsin (Rh1). Heads refers to membranes before immunoprecipitation. As a negative control for antibody and immunoprecipitation specificity, immunoprecipitations from inaD nulls did not precipitate TRP, PKC or PLC (data not shown).

Figure 3B:
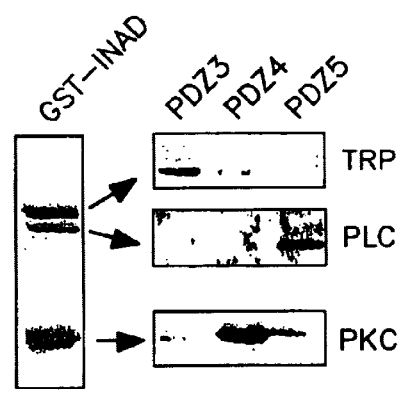
FIG. 3B shows the results obtained in vitro using a full length GST-INAD fusion protein. Full length GST-INAD fusions associate with TRP, PLCβ and PKC in cell extracts.

FIG. 3B shows similar results obtained in vitro using a full length GST-INAD fusion protein. Full length GST-INAD (N-GST—INAD-C) fusions associate with TRP, PLC$\beta$ and PKC in cell extracts.

To define the site on INAD that interacts with TRP, eye-PKC and PLC$_?$, the inventors dissected INAD. The inventors produced individual PDZ domains of INAD as GST-fusion proteins and assayed each domain for interaction with each of target proteins from whole retinal extracts.

FIG. 3B also shows that the third PDZ domain of INAD is specific for TRP[37], while the fourth domain specifically interacts with eye-PKC and the fifth domain specifically interacts with PLC$_?$. Overexpression of each of the individual PDZ domains from INAD as GST-PDZ fusions (N-GST—PDZ 1, 2, 3, 4 or 5-C) produce highly preferred interactions in biochemical assays. PDZ 1, 2, 3, 4 or 5 are shown in FIG. 2.

These results demonstrate that loss of one PDZ domain and its corresponding signal transduction protein from a transducisome does not prevent binding of the other signal transduction proteins to other PDZ domains or a transducisome protein. Immunoprecipitation of INAD from trp mutants, PLC$\beta$ nulls (norpA), or PKC nulls (inaC) still co-precipitates the remaining two targets. These results demonstrate some important aspects of transducisome and PDZ domain function. First, different PDZ domains can have different and highly specific targets. Second, INAD functions as a modular multivalent PDZ protein interacting with different components of the same pathway. Third, the transducisome complex, with signal transduction proteins bound to it, does not require binding interactions between the different signal transduction proteins.

These results are surprising because previous work only showed that INAD can associate with individual components of the phototransduction cascade[37-39], rather than the formation of a complex that organizes signal transduction proteins of a membrane. This is the first demonstration that transducisomes exist as PDZ domain containing proteins to mediate protein-protein interactions and the assembly of transduction complexes with multiple types of signal transduction proteins in the bound in the same complex.

Example 4

Transducisomes Permit or Enhance Signal Transduction and Transducisome Assembly In Vivo To investigate the function of transducisomes in signal transduction in vivo, the inventors isolated new inaD mutant alleles responsible for the dominant negative phenotype of photoreceptor deactivation and tested their corresponding proteins for the ability to assemble transducisomes and perform signal transduction in vivo.

If INAD functions in vivo as a scaffold to localize or assemble multiple components of the phototransduction cascade into transducisomes, then a null inaD mutant should display a complete loss of signaling complexes and a redistribution of individual signaling molecules. Unfortunately, only a single inaD mutant allele had been isolated and it behaved genetically and physiologically as a partially dominant negative mutation[35,36]. The inventors isolated new inaD alleles.

Using flies, the screening strategy was based on the loss of INAD antigen on immunoblots rather than on a hypothetical physiological or behavioral phenotype. Fly stocks containing individual homozygous mutagenized second chromosomes (inaD maps to the second chromosome at position 59B1-2) were generated and each stock was then subjected to immunoblot analysis for the loss of anti-INAD immunoreactivity[33]. Analysis of 2847 lines yielded two alleles, inaD[1] and inaD[2]. inaD[1] has a complete loss of the protein, while inaD[2] expresses reduced levels of protein.

Using the polymerase chain reaction (PCR), the inventors isolated the inaD gene from each mutant allele and determined their entire nucleotide sequence. inaD[1] has an amber non-sense mutation at position 811, leading to premature termination of the polypeptide chain at amino acid residue 270 (see FIG. 2 and SEQUENCE ID LISTING). This represents a complete null allele. inaD[2] has a A→G change at nucleotide 1814, leading to the substitution of a conserved glycine for glutamic acid in the fifth PDZ domain (see FIG. 2). Nucleotide positions are based on the published nucleotide sequence of INAD, Shieh and Niemeyer Neuron 14, 201–210 (1995), herein incorporated by reference.

The inventors then used immunofluorescent staining of frozen tissue sections to test for the subcellular localization of signaling molecules in the inaD[1] null mutant cells. The data demonstrate that TRP, PLC$_\beta$, and eye-PKC are completely mislocalized in the inaD[1] mutant. These signal transduction proteins no longer localize to the rhabdomeres, but instead are found randomly distributed either throughout the plasma membrane (TRP) or the cytoplasm (PLC$_\beta$ and eye-PKC). In contrast, rhodopsin, Gq$_a$ and TRPL distribute normally in inaD[1]. Immunofluorescent staining was performed on one micron thick cross-sections of wild type (showing localization), and inaD[1] mutant (no localization of signal transduction proteins as described herein) photoreceptors for different transduction proteins. No INAD-immunoreactive material was found in inaD[1] mutants.

Figure 4:
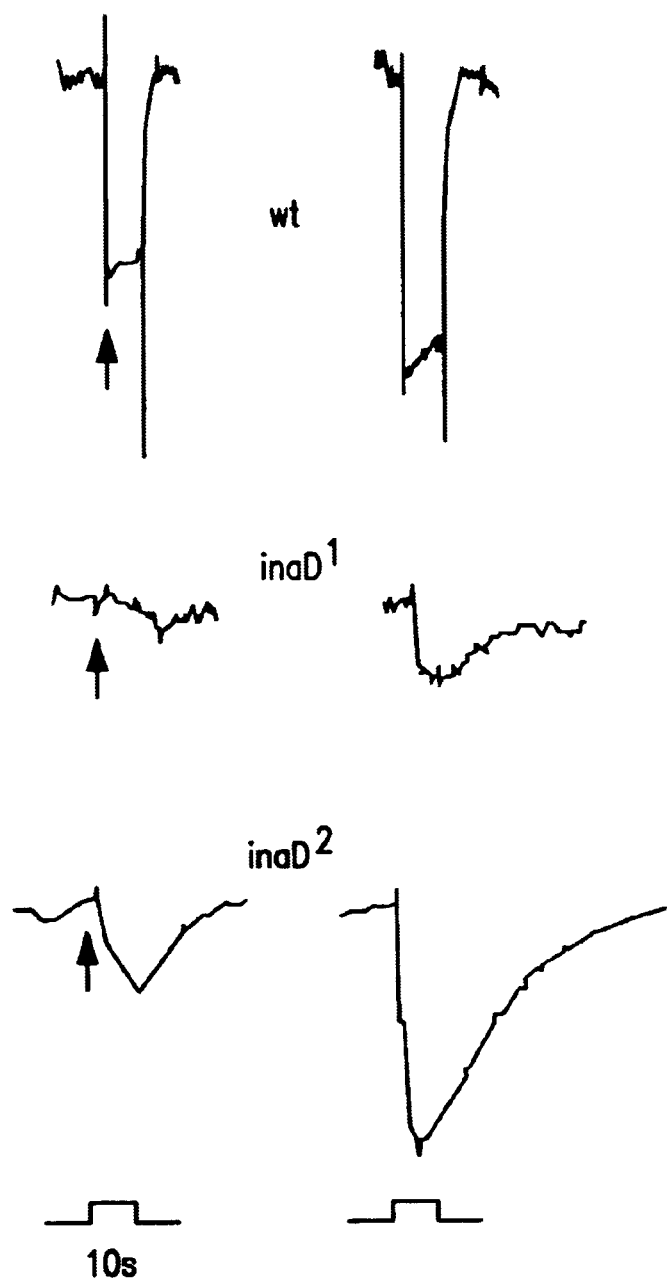
FIG. 4 shows electrophysiology recordings with altered kinetics from wildtype and mutant INAD protein in cells.

To investigate the ability of transducisomes to permit or enhance signal transduction of photoreceptors, the inventors performed electrophysiological recordings on photoreceptor cells from wildtype, inaD[1], and inaD[2] flies. Wildtype cells, with a functional transducisome, showed enhanced signal transduction in response to light compared to inaD[1] mutants. inaD[1] mutants, compared to wildtype, are much less sensitive to light, responding only at the highest light intensities and with profoundly altered kinetics (see FIG. 4). InaD[2] mutants, compared to wildtype, are less sensitive to light, but more sensitive to light compared to inaD[1] mutants, and have intermediate kinetics (see FIG. 4). The electroretinograms (ERG) recordings are from wild type (wt), inaD[1] and inaD[2] mutant flies at <1 day after eclosion. Stimulus was a 10 second pulse of orange light (570 nm longpass filter). Right traces show responses to 10x the amount of light in the left traces (log[I]=−2 log[I]=−1, respectively). Arrows indicate the onset of the stimulus. Both mutants have an increase in loss of responsiveness as a function of age.

These results demonstrate that when transducisomes are not formed in inaD[1] mutants, which have severe truncation of the tranducisome protein, extraordinary defects in phototransduction occur. Conversely, when the transducisome is functional, as in the wild type normal signal transduction is permitted. Thus, the transducisomes permit normal signal transduction to occur and enhance signal transuction compared to signal transduction by signal transduction proteins that are not complexed. InaD[2] mutants, which have point mutation of a conserved amino acid in a PDZ domain of a tranducisome protein, displayed intermediate defects in phototransduction, consistent with the role of transducisomes enhancing and organizing signal transduction.

To investigate the affect of the loss transducisome scaffolding or localization on signal transduction proteins, the inventors examined the instability of the signal transduction proteins. The inventors assayed the steady-state levels of signal transduction proteins by immunoblot analysis at different stages post-eclosion. The levels of TRP, PLC$_\beta$ and eye-PKC are all markedly reduced in the inaD[1] mutants, and by 10 days post-eclosion are less than 10% of wild type levels. In contrast, the levels of rhodopsin, Gα and TRPL are unaffected. Immunoblot analysis of transduction proteins were performed in wild type and inaD mutants. Protein levels were measured at approximately 24 hrs or sooner, after eclosion (0d) and 10 days (10d). Levels of all signal transduction proteins in wild type flies remained constant with age, while TRP, eye-PKC, and PLC declined drastically in inaD[1] mutants. Only TRP declines in inaD[215] (PDZ3), and only PLC declines in inaD[2] (PDZ5). The equivalent of one fly head per lane was run for wild type and inaD[215], and two fly heads for inaD[1] and inaD[2].

These results demonstrate a role for transducisomes for organizing signal transduction complexes, enhancing signal transduction, permitting normal signal transduction, and improving the intracellular stability of the signal transduction proteins.

Example 5

Mutations in Transducisomes Lead to Signal Transduction Destabilization and Decreased Signal Transduction To further investigate the role of transducisomes in signal transduction, the inventors assessed the affect of mutations of the INAD protein on signal transduction and signal transduction protein stability. As described herein, INAD interacts with multiple components of the phototransduction cascade and is essential for the assembly of signaling complexes, i.e. transducisomes. The inventors therefore postulated that mutation of the PDZ domain for a particular target should prevent the recruitment of that protein into the transduction complexes. This should generate in vivo phenotypes that resemble mutations in the target proteins.

The original inaD allele, inaD[215], has a missense mutation in the third PDZ domain[36]. Since this domain is involved in the interaction of INAD with TRP, as described herein, and this mutation abolishes the interaction of TRP with INAD[37,39] the stability of TRP, its subcellular localization and its function might be disrupted in inaD[215] mutants. The inventors examined TRP protein levels by immunoblot analysis, TRP subcellular localization by immunofluorescent staining of tissue sections and its function by performing whole-cell voltage-clamp recordings and electroretinograms (ERG).

TRP protein levels decline with age in inaD[215] mutants. In young inaD[215] flies (less than 24 hours old), TRP levels are indistinguishable from control flies. However, by 10 days the protein is barely detectable in immunoblots. In contrast, PLCβ, eye-PKC, and other transduction protein levels remain constant in either mutant. TRP channels are also completely mislocalized in the inaD[215] mutant, and are found randomly distributed throughout the plasma membrane (newly assayed eclosed flies to prevent degradation of TRP), while PLC is mislocalized in inaD[2] mutants. Immunofluorescent staining for TRP, eye-PKC, and PLC was conducted in one micron thick cross-section of inaD[215] and inaD[2] mutant photoreceptors.

To examine the mislocalization of TRP in more detail, ImmunoEM staining was conducted using gold-conjugated secondary antibodies. These studies confirmed and extended the immunofluorescence observations: the TRP channel randomly localizes to the plasma membrane in such mutants. The inventors found no evidence for mislocalization of any other phototransduction protein, including PLC$_\beta$ and eye-PKC in inaD[215] mutants. In wild type photoreceptors, TRP is present at significantly higher levels and exclusively in the microvillar membranes of the rhabdomeres. In inaD[215], TRP levels are significantly reduced in the rhabdomeres (newly enclosed flies) and TRP prominently distributed throughout the plasma membrane.

These results are surprising, as in contrast to Chevesich et al.[39], TRP was never found in the extracellular matrix, nor were significant levels of cytoplasmic labeling observed. The results also demonstrate that transducisomes are important for organizing signal transduction in the correct membrane and in specific regions of the cell, e.g., a region specialized for signal transduction.

Figure 5A:
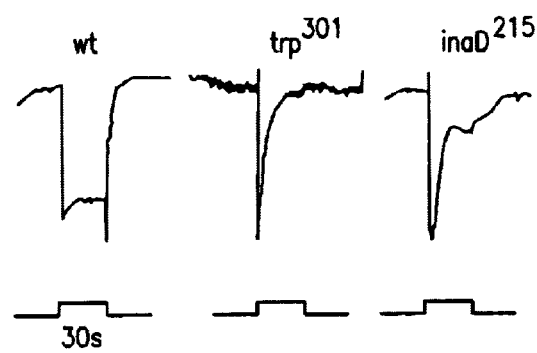
FIGS. 5A-C show altered kinetics and quantal bumps in photoreceptor cells.

To characterize the physiology of inaD[215] mutants immunoblot and ERG studies were performed. inaD[215] mutants display an ERG phenotype that approaches that of trp mutants, and does so on a time course similar to that of the decay of TRP protein seen in immunoblots. Whole-cell voltage-clamp recordings of macroscopic currents and quantum bumps were also recorded. inaD[215] mutants were originally characterized as displaying slow deactivation kinetics in response to a flash of light[36] (see FIG. 5A). ERG recordings were from wildtype, trp[301], and inaD[215] mutant eyes at 10 days after eclosion. Light stimulus was a 30 sec. pulse of orange light (570 nm longpass filter). Note the transient response of trp mutants (trp=transient receptor potential), and older inaD[215] flies.

Figure 5B:
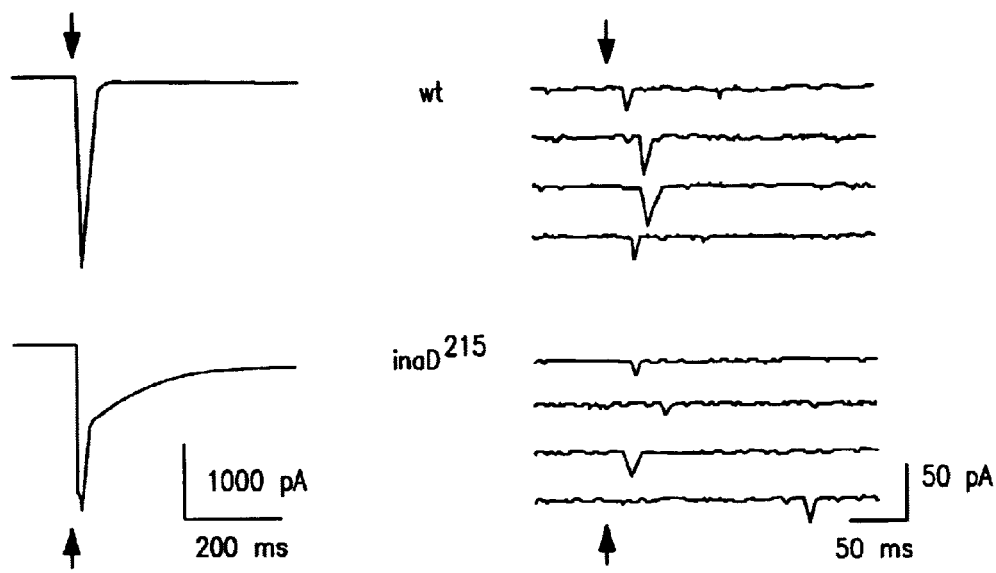

To determine the basis for the slow deactivation component in inaD[215] photoreceptors, quantal responses were characterized. In wild-type photoreceptors, single-photons give rise to unitary events known as quantum bumps[41,42]. Quantum bumps are the result of the activation of a single rhodopsin molecule and reflect the amplification of the entire signaling pathway, leading to the opening of the light-activated channels[43]. Surprisingly, the quantum bumps from inaD[215] flies display normal termination kinetics (wild type $t_{90\%}$=13.6±0.58 ms, inaD[215]$t_{90\%}$=13.8±0.60 ms; FIG. 5B, right panel), indicating that the macroscopic defect of inaD[215] mutants cannot be due to an underlying defect in deactivation. FIG. 5B shows whole-cell recordings (left traces) and quantum bumps (right traces) from wild type (wt) and inaD[215] mutant photoreceptors.

Figure 5C:
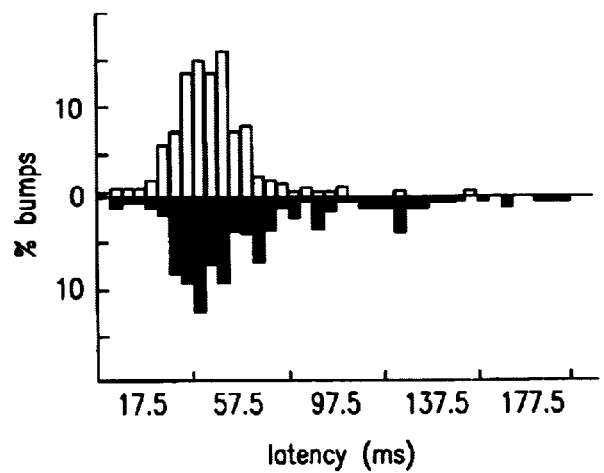

For macroscopic responses, cells were stimulated (arrow) with a 10 ms flash of 580 nm light of log[I]=−1. The deactivation time course of inaD[215] is well fit by the sum of two exponentials (time constants of 14.7±2.5 and 143.1±12.1 ms; N=7), while the time course of decay of wild type responses is fitted by a single exponential with a time constant of 14.5±2.2 ms (N=6). For quantum bumps[44], cells were stimulated with a 10 ms flash of 580 nm light of log[I]=−6.5 (arrow). This stimulus produced a probability of not seeing a bump of 0.40 in wild type and 0.65 in inaD$^{215}$. Note the normal termination kinetics of inaD$^{215}$ bumps. inaD$^{215}$ quantum bumps have defective latency. Latency to first bump from wild type (open bars) and inaD$^{215}$ mutant (solid bars) were 47.6±1.3 ms (N=210 bumps from 7 cells), and 67.0±3.1 ms (N=160 bumps from 7 cells), respectively. Instead of defective termination kinetics, the mean latency times between stimulus and quantum bump generation were significantly altered in inaD$^{215}$ mutants (47.6±1.3 ms in wild type vs. 67.0±3.2 ms in inaD$^{215}$; FIG. 5C). Thus, inaD$^{215}$ photoreceptors do not have a defect in termination[36], nor do they display problems with feedback regulation[37,39]. The phenotype is consistent with the mislocalization of TRP channels that leads to longer latencies and a corresponding macroscopic defect in deactivation kinetics. Again these results are surprising, as previous work postulated that deactivation related INAD might be due to an affect TRP channel activity[37-39], rather than affecting TRP localization or stability while maintaining channel activity.

To further define the physiological importance of the interaction between INAD and its individual targets, the interaction between INAD and PLC$_\beta$ was also studied. PLC$_?$ is randomly distributed in the cytoplasm of inaD$^2$ photoreceptor cells, which has mutation in the fifth PDZ domain (see FIG. 2) of INAD. inaD$^2$ mutation failed to affect the distribution of other signal transduction proteins like eye-PKC, TRP, Rh1 and DGq. These results from fly eyes are consistent with the specific redistribution of PLC$_\beta$ in vivo due to inaD$^2$ mutant photoreceptors and a failure of PLC$_\beta$ to be recruited into mutant transducisomes, which leads to PLC$_\beta$ instability and a decay of PLC$_\beta$ over time.

The loss of PLC$_\beta$ from transduction complexes, leads to significant defects in phototransduction. ERG recordings from inaD$^2$ mutant photoreceptors exhibit major defects in response kinetics: latency, activation, and deactivation, which are all significantly slower in the mutant cells. Because these recording were carried out in newly enclosed flies, a time at which there are near normal levels of PLC as described herein, these findings clearly illustrate that it is not the mere presence of a transducisome, but rather its location that promotes effective signaling. Taken together data validate the existence of a highly organized signaling unit, a transducisome, demonstrate that it is possible to experimentally manipulate the composition of signaling complexes, and substantiate the essential role of PDZ domains in the assembly and function of signal transduction complexes in vivo.

Example 5

A GPCR Based Screen for Modulators of Signal Transduction Function

A screen for identifying modulators of signal transduction was designed using cells that can express a GPCR, a phospholipaseC, and a G protein that assemble into a transducisome. A cell line containing Gq-type GPCR receptor that expresses β-lactamase in response to the addition of the agonist was produced by FACS selection. The Gαq protein was endogenously expressed. The activation response is inhibited by an antagonist. Jurkat clones expressing NFAT-β1a, as described in Negulescu et al filed Jun. 19, 1997 herein incorporated by reference) were transfected with expression vectors containing the Gq receptor and neomycin resistance gene (double transfection). The transfected population was neo-selected and sorted by FACS for clones responding to the GPCR agonist. Cells were stimulated for three hours with the indicated ligands. Cells were then loaded with β-lactamase substrate CCF2/ac2AM for 1 hour, washed, dispensed into wells of a microtiter plate (100,000 cells/well) and the blue/green ratio was recorded by a plate reader.

A twenty-fold change in signal upon receptor activation with an agonist (saturating dose 100 µM) was observed. A receptor antagonist (10 µM) completely inhibited the agonist activation of the receptor.

To identify modulators of signal transduction using a transducisome these cells are transfected with a polynucleotide encoding a transducisome protein that comprises individual PDZ domains that assemble such transducisome. Expression of transducisome protein enhances signal transduction to provide for better signals due to increased β-lactamase expression and activity. Controls for the affect of transducisome protein on signal transduction can also be used to identify modulators of transducisome protein/signal transduction protein interactions. Such controls include mutant or truncated transducisome protein that fails to functionally bind the signal transduction protein that is normally part of a transducisome complex or cells not expressing transducisome proteins from exogenous or mutated polynucleotides (e.g., non-induced polynucleotide having expression controlled by an inducable promoter, defective transducisome proteins due to a mutation or non-transfected cells). Test compounds are added in the presence or absence of agonist, antagonist, inverse agonist or other known modulators.

Example 6

An Ion Channel Based Screen for Modulators of Signal Transduction Function

A screen for identifying modulators of signal transduction was designed using cells that can express rhodospin, an ion channel that binds a transducisome protein, and a phospholipase that binds a transducisome protein, a PKC that binds a transducisome protein and a transducisome protein. Cells are maintained in the dark and exposed for a predetermined time to light at a wavelength that will activate rhodospin that in turn activates Gqα. The G-protein in turn activates PLCβ leading to the increase of inositol triphosphate and diacylglycerol that lead to the activation of ion channel, TRP. Ion channel activity is monitored with voltage sensitive dyes using a fluorimeter. Test compounds can be added before or after light activation.

Example 7

A FRET Based Screen for Modulators of Transducisome Protein Binding to Signal Transduction Proteins A screen for identifying modulators of transducisone binding was designed using cells that can express modified GFP FRET partners fused to transducisome fragments and modified GFP FRET partners fused to signal transduction proteins that bind to the corresponding transducisome fragment. Polynucleotides encoding a first modified GFP partner fused to an INAD protein containing a PDZ5. The resulting fusion protein is oriented as follows: N-INAD-C-N-GFP FRET partner-C; wherein N is the n-terminus of each respective fragment and C is the c-terminus of each respective fragment. Polynucleotides encoding a second modified GFP partner fused to a PLCβ protein containing a PDZ5. The resulting fusion protein is oriented as follows: N-GFP FRET-partner-C-N-PLCβ protein-C; wherein N is the n-terminus of each respective fragment and C is the c-terminus of each respective fragment. Expression of each modified GFP fusion protein is accomplished with use of a constitutive promoter and a vector suitable for expression in CHO or insect cells. After expression of the GFP fusion proteins, FRET is measured between the modified GFP FRET partners in the presence and absence of test chemicals using a fluorimeter.

Publications

1. Schlessinger, J. SH2/SH3 signaling proteins. *Curr Opin Genet Dev* 4, 25–30 (1994).
2. Pawson, T. SH2 and SH3 domains in signal transduction. *Adv Cancer Res* 64, 87–110 (1994).
3. Lemmon, M. A., Ferguson, K. M. & Schlessinger, J. PH domains: diverse sequences with a common fold recruit signaling molecules to the cell surface. *Cell* 85, 621–624 (1996).
4. Shaw, G. The pleckstrin homology domain: an intriguing multifunctional protein module. *Bioessays* 18, 35–46 (1996).
5. Harrison, S. C. Peptide-surface association: the case of PDZ and PTB domains. *Cell* 86, 341–343 (1996).
6. van der Geer, P & Pawson, T. The PTB domain: a new protein module implicated in signal transduction. *Trends Biochem Sci* 20, 277–280 (1995).
7. Kavanaugh, W. M., Turck, C. W. & Williams, L. T. PTB domain binding to signaling proteins through a sequence motif containing phosphotyrosine. *Science* 268, 1177–1179 (1995).
8. Woods, D. F. & Bryant, P. J. The discs-large tumor suppressor gene of *Drosophila* encodes a guanylate kinase homolog localized at septate junctions. *Cell* 66, 451–464 (1991).
9. Cho, K. O., Hunt, C. A. & Kennedy, M. B. The rat brain postsynaptic density fraction contains a homolog of the *Drosophila* discs-large tumor suppressor protein. *Neuron* 9, 929–942 (1992).
10. Woods, D. F. & Bryant, P. J. ZO-1, DlGA and PSD-95/SAP90: homologous proteins in tight, septate and synaptic cell junctions. *Mech Dev* 44, 85–89 (1993).
11. Kennedy, M. B. Origin of PDZ (DHR, GLGF) domains. *Trends Biochem Sci* 20, 350 (1995).
12. Kornau, H. C., Schenker, L. T., Kennedy, M. B. & Seeburg, P. H. Domain interaction between NMDA receptor subunits and the postsynaptic density protein PSD-95. *Science* 269, 1737–40 (1995).
13. Saras, J. & Heldin, C. H. PDZ domains bind carboxy-terminal sequences of target proteins. *Trends Biochem Sci* 21, 455–458 (1996).
14. Sheng, M. & Kim, E. Ion channel associated proteins. *Curr Opin Neurobiol* 6, 602–608 (1996).
15. Sheng, M. PDZs and receptor/channel clustering: rounding up the latest suspects. *Neuron* 17, 575–578 (1996).
16. Muller, B. M., et al. SAP102, a novel postsynaptic protein that interacts with NMDA receptor complexes in vivo. *Neuron* 17, 255–265 (1996).
17. Niethammer, M., Kim, E. & Sheng, M. Interaction between the C terminus of NMDA receptor subunits and multiple members of the PSD-95 family of membrane-associated guanylate kinases. *J Neurosci* 16, 2157–2163 (1996).
18. Kim, E., Cho, K. O., Rothschild, A. & Sheng, M. Heteromultimerization and NMDA receptor-clustering activity of Chapsyn-110, a member of the PSD-95 family of proteins. *Neuron* 17, 103–113 (1996).
19. Kim, E., Niethammer, M., Rothschild, A., Jan, Y. N. & Sheng, M. Clustering of Shaker-type K+ channels by interaction with a family of membrane-associated guanylate kinases. *Nature* 378, 85–88 (1995).
20. Kim, E. & Sheng, M. Differential K+ channel clustering activity of PSD-95 and SAP97, two related membrane-associated putative guanylate kinases. *Neuropharmacology* 35, 993–1000 (1996).
21. Cohen, N. A., Brenman, J. E., Snyder, S. H. & Bredt, D. S. Binding of the inward rectifier K+ channel Kir 2.3 to PSD-95 is regulated by protein kinase A phosphorylation. *Neuron* 17, 759–767 (1996).
22. Kim, E., et al. GKAP, a novel synaptic protein that interacts with the guanylate kinase-like domain of the PSD-95/SAP90 family of channel clustering molecules. *J Cell Biol* 136, 669–678 (1997).
23. Brenman, J. E., et al. Interaction of nitric oxide synthase with the postsynaptic density protein PSD-95 and alphal-syntrophin mediated by PDZ domains. *Cell* 84, 757–767 (1996).
24. Budnik, V., et al. Regulation of synapse structure and function by the *Drosophila* tumor suppressor gene dlg. *Neuron* 17,627–640 (1996).
25. Brenman, J. E., Christopherson, K. S., Craven, S. E., McGee, A. W. & Bredt, D. S. Cloning and characterization of postsynaptic density 93, a nitric oxide synthase interacting protein. *J Neurosci* 16, 7407–7415 (1996).
26. Sato, T., Irie, S., Kitada, S. & Reed, J. C. FAP-1: a protein tyrosine phosphatase that associates with Fas. *Science* 268, 411–415 (1995).
27. Doyle, D. A., et al. Crystal structures of a complexed and peptide-free membrane protein-binding domain: molecular basis of peptide recognition by PDZ. *Cell* 85, 1067–1076(1996).
28. Cabral, J. H., et al. Crystal structure of a PDZ domain. *Nature* 382, 649–652 (1996).
29. Fanning, A. S. & Anderson, J. M. Protein-protein interactions: PDZ domain networks. *Curr Biol* 6, 1385–1388 (1996).
30. Ranganathan, R., Malicki, D. M. & Zuker, C. S. Signal Transduction in *Drosophila* Photoreceptors. *Annual Review of Neuroscience* 18, 283–317 (1995).
31. Suzuki, E., Katayama, E. & Hirosawa, K. Structure of photoreceptive membranes of *Drosophila* compound eyes as studied by quick-freezing electron microscopy. *Journal of Electron Microscopy* 42, 178–184 (1993).
32. Pak, W. L. *Drosophila* in vision research. The Friedenwald Lecture. *Invest Ophthalmol Vis Sci* 36, 2340–2357 (1995).
33. Niemeyer, B. A., Suzuki, E., Scott, K., Jalink, K. & Zuker, C. S. The *Drosophila* Light-Activated Conductance is Composed of the Two Channels TRP and TRPL. *Cell* 85, 651–659 (1996).
34. Smith, D. P., et al. Photoreceptor deactivation and retinal degeneration mediated by a photoreceptor-specific protein kinase C. *Science* 254, 1478–1484 (1991).
35. Pak, W. L. *Mutants affecting the vision in Drosophila melanogaster* 1-703–733 (Plenum, New York/London, 1975).
36. Shieh, B.-H. & Niemeyer, B. A novel protein encoded by the InaD gene regulates recovery of visual transduction in *Drosophila*. *Neuron* 14, 201–210 (1995).
37. Shieh, B. H. & Zhu, M. Y. Regulation of the TRP Ca2+ channel by INAD in *Drosophila* photoreceptors. *Neuron* 16, 991–998 (1996).

38. Huber, A., et al. The transient receptor potential protein (Trp), a putative store-operated Ca2+ channel essential for phosphoinositide-mediated photoreception, forms a signaling complex with NorpA, InaC and InaD. *Embo J* 15, 7036–7045 (1996).
39. Chevesich, J., Kreuz, A. J. & Montell, C. Requirement for the PDZ domain protein, INAD, for localization of the TRP store-operated channel to a signaling complex. *Neuron* 18, 95–105 (1997).
40. Songyang, Z., et al. Recognition of unique carboxyl-terminal motifs by distinct PDZ domains. *Science* 275, 73–77 (1997).
41. Yeandle, S. Studies on the slow potential and the effect of cation on the electrical responses of the Limulus ommatidium. Ph. D. Thesis (Johns Hopkins Univ., 1957).
42. Baylor, D. A., Lamb, T. D. & Yau, K.-W. Responses of retinal rods to single photons. *Journal of Physiology* 288, 613–634 (1979).
43. Minke, B. Is the Receptor Potential of Fly Photoreceptors a Summation of Single-Photon Responses? *Comments Theoretical Biology* 3, 229–263 (1994).
44. Scott, K., Leslie, A., Sun, Y., Hardy, R. & Zuker, C. Gaq Protein Function in vivo: Genetic Dissection of Its Role in Photoreceptor Cell Physiology. *Neuron* 15, 919–927 (1995).
45. Marcus, S., Polverino, A., Barr, M. & Wigler, M. Complexes between STE5 and components of the pheromone-responsive mitogen-activated protein kinase module. *Proc Natl Acad Sci U S A* 91, 7762–7766 (1994).
46. Printen, J. A. & Sprague, G. J. Protein-protein interactions in the yeast pheromone response pathway: Ste5p interacts with all members of the MAP kinase cascade. *Genetics* 138, 609–619 (1994).
47. Choi, K. Y., Satterberg, B., Lyons, D. M. & Elion, E. A. Ste5 tethers multiple protein kinases in the MAP kinase cascade required for mating in *S. cerevisiae*. *Cell* 78, 499–512 (1994).
48. Larrivee, D. C., Conrad, S. K., Stephenson, R. S. & Pak, W. L. Mutation that selectively affects rhodopsin concentration in the peripheral photoreceptors of *Drosophila melanogaster*. *Journal of General Physiology* 78, 521–545 (1981).
49. Johnson, E. & Pak, W. Electrophysiological study of *Drosophila rhodopsin* mutants. *Journal of General Physiology* 88, 651–73 (1986).
50. Hualing, D., et al. GRIP: a synaptic PDZ domain-containing protein that interacts with AMPA receptors. *Nature* 386, 279–284 (1997).

All publications, including patent documents and scientific articles, referred to in this application are incorporated by reference in their entirety for all purposes to the same extent as if each individual publication were individually incorporated by reference.

---

We claim:

1. A method of identifying a modulator of signal transduction affected by an Inactivation No Afterpotential D (InaD) protein, comprising:
   a) contacting a first cell with a test chemical,
      wherein said first cell comprises at least one signal transduction protein and a polynucleotide encoding a transducisome protein, and said transducisome protein functionally binds to said signal transduction protein to permit or enhance signal transduction, and wherein the transducisome protein is InaD,
   b) activating said signal transduction in said first cell,
   c) detecting said signal transduction from said first cell with a signal transduction detection system,
   d) contacting a second cell with said test chemical,
      wherein said second cell comprises said signal transduction protein and a polynucleotide encoding a defective InaD protein that fails to functionally bind at least one signal transduction protein to permit or enhance signal transduction, and wherein the defective InaD protein comprises an amino acid mutation in a PDZ domain other than an inaD$^{215}$ mutation,
   e) activating said signal transduction in said second cell,
   f) detecting said signal transduction from said second cell with a signal transduction detection system, and
   g) comparing said signal transduction from said first cell with signal transduction from said second cell, wherein a difference in detected signal transduction from said first cell and said second cell identifies said test chemical as a modulator of signal transduction affected by InaD.

2. The method of claim 1, wherein said second cell is the same type of cell as said first cell.

3. The method of claim 1, wherein the signal transduction protein is a kinase, a phosphatase, a G-protein coupled receptor (GPCR), a tyrosine kinase receptor, a tyrosine phosphatase receptor, an ion channel, a G-protein, a phospholipase or a calcium binding protein.

4. The method of claim 3, wherein said signal transduction protein is transient receptor potential protein (TRP), protein kinase C, or phospholipase C.

5. The method of claim 1, wherein the amino acid mutation of said defective InaD is in the first, second, fourth, or fifth PDZ domain.

6. The method of claim 1, wherein the amino acid mutation of said defective InaD is in the second, fourth, or fifth PDZ domain.

7. The method of claim 1, wherein the amino acid mutation of said defective InaD is an inaD$^2$ or an inaD$^1$ mutation.

8. The method of claim 1, wherein the amino acid mutation of said defective InaD is in the third PDZ domain and signal transduction is activated with light and detected by detecting an altered latency period.

9. The method of claim 1, further comprising:
   h) contacting a third cell with said test chemical, wherein said third cell comprises said signal transduction protein and a polynucleotide encoding a defective InaD, said defective InaD fails to functionally bind at least one signal transduction protein to permit or enhance signal transduction, and wherein said defective InaD of said third cell comprises a mutation in a PDZ domain, and said defective InaD of said second cell comprises a mutation in a different PDZ domain,
   i) activating said signal transduction in said third cell,
   j) detecting said signal transduction from said third cell with a signal transduction detection system, and k) comparing signal transduction from said first cell with signal transduction from said second cell and signal transduction from said third cell, wherein a difference in detected signal transduction between said second cell and said third cell is informative of the signal transduction pathway affected by the modulator.

10. A method of identifying a modulator of signal transduction affected by Inactivation No Afterpotential D (InaD), comprising:

a) contacting a first cell with a test chemical,
   wherein said first cell comprises at least one signal transduction protein and a polynucleotide encoding a transducisome protein, and said transducisome protein functionally binds to said signal transduction protein to permit or enhance signal transduction, and wherein said transducisome protein is an InaD polypeptide of SEQ ID NO:1, b) activating said signal transduction in said first cell, c) detecting said signal transduction from said first cell with a signal transduction detection system, d) contacting a second cell with said test chemical,
   wherein said second cell comprises said signal transduction protein and a polynucleotide encoding a defective InaD, said defective InaD fails to functionally bind at least one signal transduction protein to permit or enhance signal transduction or said second cells fails to express said InaD polypeptide to permit said InaD polypeptide to functionally bind to at least one signal transduction protein to permit or enhance signal transduction, e) activating said signal transduction in said second cell, f) detecting said signal transduction from said second cell with a signal transduction detection system, and g) comparing said signal transduction from said first cell with signal transduction from said second cell, wherein a difference in detected signal transduction from said first cell and said second cell identifies said test chemical as a modulator of signal transduction affected by InaD.

* * * * *